(12) United States Patent
Barron et al.

(10) Patent No.: US 7,713,970 B2
(45) Date of Patent: May 11, 2010

(54) SUBSTITUTED CYCLIC UREA DERIVATIVES

(75) Inventors: Edward J. Barron, Trenton, NJ (US);
Larry Y. Zhang, Kendall Park, NJ (US);
John W. Lyga, Basking Ridge, NJ (US);
Matthew P. Whiteside, Morrisville, PA (US)

(73) Assignee: FMC Corporation, Philadelphia, PA (US)

( * ) Notice: Subject to any disclaimer, the term of this patent is extended or adjusted under 35 U.S.C. 154(b) by 304 days.

(21) Appl. No.: 11/569,188

(22) PCT Filed: May 18, 2005

(86) PCT No.: PCT/US2005/017993
§ 371 (c)(1),
(2), (4) Date: Dec. 11, 2007

(87) PCT Pub. No.: WO2005/112941
PCT Pub. Date: Dec. 1, 2005

(65) Prior Publication Data
US 2008/0200518 A1   Aug. 21, 2008

Related U.S. Application Data

(60) Provisional application No. 60/572,196, filed on May 18, 2004.

(51) Int. Cl.
*C07D 233/32* (2006.01)
*C07D 249/12* (2006.01)
*C07D 253/06* (2006.01)
*A61K 31/4166* (2006.01)
*A61K 31/4196* (2006.01)
*A61K 31/513* (2006.01)

(52) U.S. Cl. ........................ 514/242; 514/382; 514/392; 514/384; 544/182; 548/251; 548/262.2; 548/316.7

(58) Field of Classification Search ........................ None
See application file for complete search history.

(56) References Cited

U.S. PATENT DOCUMENTS

| | | | |
|---|---|---|---|
| 4,338,317 A | 7/1982 | Temple, Jr. et al. | |
| 4,487,773 A | 12/1984 | Temple, Jr. et al. | |
| 5,952,386 A | 9/1999 | Matsuo et al. | |
| 6,294,573 B1 | 9/2001 | Curtin et al. | |
| 6,706,739 B2 | 3/2004 | Shia et al. | |
| 6,987,194 B2 | 1/2006 | Theodoridis et al. | |
| 7,208,450 B2 | 4/2007 | Theodoridis et al. | |
| 2003/0073847 A1 | 4/2003 | Sakamoto et al. | |
| 2005/0159599 A1 | 7/2005 | Itoh et al. | |
| 2006/0094776 A1 | 5/2006 | Theodoridis et al. | |
| 2006/0247283 A1 | 11/2006 | Theodoridis et al. | |
| 2006/0270726 A1 | 11/2006 | Theodoridis et al. | |

FOREIGN PATENT DOCUMENTS

WO        WO 03/074498 A1    9/2003

OTHER PUBLICATIONS

"Side Reactions in Organic Synthesis: A Guide to Successful Synthesis Design", Wiley-VCH Verlag GmbH & Co. KGaA, Weinheim, pp. 1-16 (2005).*
Shia, K.-S., et al., "Design, Synthesis, and Structure—Activity Relationship of Pyridyl Imidazolidinones: A Novel Class of Potent and Selective Human Enterovirus 71 Inhibitors," *J. Med. Chem.* 45:1644-1655, American Chemical Society (2002).
International Search Report for International Application No. PCT/US05/17993, ISA/US, Alexandria, VA, mailed on Sep. 21, 2006.

* cited by examiner

*Primary Examiner*—Kamal A Saeed
*Assistant Examiner*—Michael Barker

(57) ABSTRACT

Certain novel phenyl substituted cyclic urea derivatives have unexpected insecticidal activity. These compounds are represented by formula I: where A, B a, D, b, E, G, c, d, J, X and R through $R^{10}$, inclusively, are fully described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

19 Claims, No Drawings

SUBSTITUTED CYCLIC UREA DERIVATIVES

This application claims the benefit of U.S. Provisional Application No. 60/572,196, filed May 18, 2004.

FIELD OF THE INVENTION

The present invention generally relates to novel compounds, processes and intermediates useful in preparing such compounds, compositions containing such compounds and the use of such compounds in controlling insects and acarids. In particular, it pertains to phenylalkyl substituted cyclic urea derivatives and agriculturally acceptable salts thereof, compositions of these insecticides and acaricides, and methods for their use in controlling insects and acarids.

BACKGROUND OF THE INVENTION

A longstanding worldwide demand exists for new, effective, less costly, and safe means to control pests in agricultural crops, greenhouse crops, nursery crops, ornamentals, turf, forestry, stored food and fiber products, structures, livestock, households, and public and animal health. Agricultural crop costs incurred by pests exceed billions of dollars annually in decreased crop yields, reduced crop quality and increased harvesting costs. Agricultural crops include wheat, corn, soybeans, potatoes, and cotton to name a few. Soil-bourne insects, such as termites and white grubs, cause millions of dollars of damage to structures, turfs and ornamentals. Household pests, such as flies, ants and cockroaches, carry disease and are undesirable in peoples' homes. In addition to these pests, many blood-feeding insects are vectors for pathogenic microorganisms that threaten human and animal health, or are annoying at the least. Insecticides and acaricides are desired which can control these pests without damaging crops, turfs, ornamentals or structures, and which have no deleterious effects to mammals and other living organisms.

A number of patents and publications disclose a variety of dihalopropene compounds that are reported to be insecticidally and acaricidally active. For example, U.S. Patent Application Publication No. 2003/0073847 discloses certain dihalopropene compounds for use as insecticides and acaricides of the general formula:

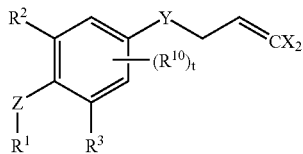

where Z is oxygen, sulfur, or $NR^4$ (wherein $R^4$ is hydrogen, or $C_1$-$C_3$ alkyl); Y is oxygen, sulfur, or NH; X's are independently chlorine or bromine; $R^2$, $R^3$, and $R^{10}$ are independently halogen, $C_1$-$C_3$ alkyl, or $C_1$-$C_3$ haloalkyl; t is an integer of 0 to 2; and $R^1$ is A-$(CR^5R^6)_p$CHR$^7$— (Q1), A-B-$(CR^5R^6)_p$CHR$^7$— (Q2), A-$(CR^{11}R^{12})_s$—B—$(CR^5R^6)_p$—CHR$^7$— (Q3), A-C($R^{13}$)=C($R^{14}$)—$(CR^5R^6)_p$—CHR$^7$— (Q4), A-B—$(CR^{11}R^{12})_s$—C($R^{13}$)=C($R^{14}$)—$(CR^5R^6)_p$—CHR$^7$— (Q5), A-B-$(CR^{11}R^{12})_s$—C(=O)—O—$(CR^5R^6)_p$—CHR$^7$— (Q6), or A-C($R^{13}$)=C($R^{14}$)—C(=O)—O—$(CR^5R^6)_p$—CHR$^7$— (Q7), where A is an optionally substituted heterocyclic ring, more particularly A is an optionally substituted 5-membered heterocyclic ring group containing 2, 3 or 4 nitrogen atoms and 1 or 2 carbon atoms; B is oxygen, $S(O)_q$, $NR^9$, $C(=G^1)G^2$ or $G^1C(=G^2)$; q is an integer of 0 to 2; $R^9$ is hydrogen, acetyl or $C_1$-$C_3$ alkyl; $G^1$ and $G^2$ are independently oxygen and sulfur; $R^5$, $R^6$, $R^7$, $R^{11}$ and $R^{12}$ are independently selected from hydrogen, $C_1$-$C_3$ alkyl, or trifluoromethyl; $R^{13}$ and $R^{14}$ are independently selected from hydrogen, $C_1$-$C_3$ alkyl, halogen or trifluoromethyl; p is an integer of 0 to 6; and s is an integer of 1 to 6.

PCT publication WO 2003074498 discloses a class of cyclic diamine compounds of the following formula useful as pesticides:

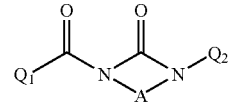

where
A is $CY_1Y_2OCY_3Y_4$, $CY_1Y_2SO_nCY_3Y_4$, $CY_1Y_2NRCY_3Y_4$, $CY_1$=$NCY_3Y_4$ or $CY_1Y_2N$=$CY_3$; R is hydrogen, optionally oxidized S, nitro, nitroso, CHO, CN, OH, amino, hydrocarbyl, heterocyclyl, $(C_2$-$C_7)$acyl, $(C_1$-$C_6)$alkoxycarbonyl, $(C_7$-$C_{11})$arylalkylcarbonyl, $(C_6$-$C_{10})$aryloxycarbonyl, carbamoyl, thiocarbamoyl, hydroxyoxalyl, aminooxalyl or hydroxyaminooxalyl (all optionally substituted);
$Q_1$ is phenyl or heteroaryl (both substituted);
$Q_2$ is substituted phenyl, $(C_1$-$C_6)$alkyl or $(C_1$-$C_6)$haloalkyl;
provided that when A is $CH_2OCH_2$ then $Q_1$ is not dichlorophenyl.

U.S. Pat. No. 5,952,386 discloses certain dihalopropene compounds with urea linkers for use as insecticides of the general formula:

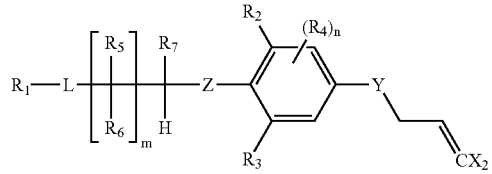

where $R_1$ is $C_1$-$C_{10}$ alkyl or the like; L is C(=O)NH, NHC(=O)NH or the like; $R_2$, $R_3$ and $R_4$ are independently halogen or the like; $R_5$, $R_6$, and $R_7$ are independently hydrogen or the like; m is an integer of 0 to 4; n is an integer of 0 to 2; X is chlorine or the like; Y is oxygen or the like; and Z is oxygen or the like.

There is no disclosure or suggestion in any of the above-referenced patents or publications of the structures and pesticidal activity of the compounds of the present invention.

SUMMARY OF THE INVENTION

In accordance with the present invention, it has now been found that certain novel substituted cyclic urea derivatives demonstrate unexpectedly improved pesticidal activity as compared with compounds described above. The improved pesticidal activity is attributed to the substituted cyclic urea linker containing the substituent identified as G below. Pesticidal activity is reduced if this urea component of the compound is not cyclic or specifically substituted as described below.

The novel substituted cyclic urea derivatives are represented by the following general formula I:

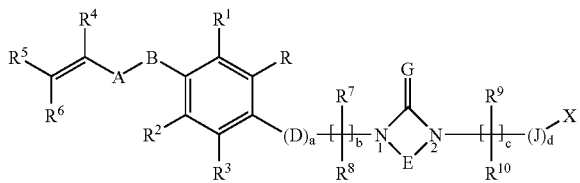

where
R and $R^3$ are independently selected from hydrogen, halogen, hydroxy, $(C_1-C_6)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=K)-L, and —C($R^{16}$)-M-$R^{17}$, wherein the optional substituent is selected from $(C_1-C_4)$alkyl, halogen, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where
K is selected from O, S, $NR^{18}$, and $NOR^8$, where $R^{18}$ is hydrogen, $(C_1-C_4)$alkyl, halo$(C_1-C_4)$alkyl, aryl and aryl$(C_1-C_4)$alkyl;
L is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;
M is selected from O, S, and $NR^{18}$, where $R^{18}$ is as previously described;
$R^{16}$ and $R^{17}$ are independently selected from hydrogen, $(C_1-C_4)$alkyl and halo$(C_1-C_4)$alkyl, and $R^{16}$ and $R^{17}$ may be taken together with -Q(CHR$^{18}$)$_e$—, where e is an integer of 2 to 4; Q is selected from O, S, and $NR^{18}$, where $R^{18}$ is as previously described;
—$R^1$ and $R^2$ are independently selected from hydrogen, halogen and $(C_1-C_3)$alkyl;
A is selected from O, S, *OCH$_2$ and (CH$_2$)$_f$ where the asterisk denotes attachment to B, and f is an integer selected from 1, 2 and 3;
B is selected from selected from CH$_2$, O, S and $NR^{19}$ where $R^{19}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo$(C_2-C_4)$alkenyl$(C_1-C_3)$alkyl, di$(C_1-C_3)$alkylphosphonate, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl; provided that A and B are not simultaneously O or S;
$R^4$ is hydrogen;
$R^5$ and $R^6$ are independently selected from halogen;
a is an integer selected from 0 or 1;
and when a is 1,
D is O, CH$_2$, OCH$_2$, CH$_2$O, OCH=CH, C(=O), S(O)$_g$, —CH=CH—, —OC(=O)—, —OC(=O)NH—,
—NHC(=O)—, —NHSO$_2$—, —N=CH—, $NR^{19}$, or N(oxide)$R^{19}$ where $R^{19}$ is as previously described, and g is an integer selected from 0, 1 or 2;
b is an integer selected from 0, 1, 2, 3, 4, 5 or 6;
and when b is 1 or more,
$R^7$ and $R^8$ are independently selected from hydrogen, halogen, $(C_1-C_4)$alkyl, cyclo$(C_3-C_6)$alkyl, halo$(C_1-C_4)$alkyl, and aryl;
E is a bridging group selected from —$CR^{20}$=$CR^{21}$—, *—$CR^{20}$=N—, *—N=$CR^{20}$—, —N=N—, *—C(=O)$CR^{20}R^{21}$, *—$CR^{20}R^{21}$C(=O)—, —($CR^{20}R^{21}$)$_n$—, *—N=$CR^{20}$C(=O), *—C(=O)$CR^{20}$=N—, *—C(=O)$NR^{20}$—, *—$NR^{20}$C(=O)—, *—$CR^{20}$=$CR^{21}$C(=O)—, *—C(=O)$CR^{21}$=$CR^{20}$—, —$CR^{20}R^{21}$OC$R^{22}R^{23}$—, —C(=))C(=))—, *—S(O)$_g$$CR^{20}R^{21}$—, *—S(O)$_g$$NR^{20}$—, *—OC$R^{22}R^{23}$—, *—$CR^{22}R^{23}$O— and —$C$(=O)— where the asterisk denotes attachment at the position designated as 1 in formula I, g is as previously described, n is an integer selected from 2, 3, and 4, and $R^{20}$ through $R^{23}$, inclusively, are independently selected from hydrogen, halogen, $(C_1-C_4)$alkyl, $(C_1-C_4)$alkoxy, $(C_1-C_4)$alkoxy$(C_1-C_4)$alkyl, halo$(C_1-C_4)$alkyl, $(C_1-C_4)$alkoxycarbonyl, nitro, cyano, amino, $(C_1-C_4)$alkylamino and aryl; and $R^{20}$ through $R^{23}$ in geminal positions may be taken together to form 5-, 6- or 7-membered spiro rings comprised of carbon, nitrogen and oxygen, or $R^{20}$ through $R^{23}$ in adjacent positions may be taken together to form 5-, 6- or 7-membered rings comprised of carbon, nitrogen and oxygen or a benzo-fused ring;
G is selected from O, S, N-Q, or C-Q, where Q is cyano or nitro;
c is an integer selected from 0, 1, 2, 3 or 4;
and when c is 1 or more,
$R^9$ and $R^{10}$ are independently selected from hydrogen, $(C_1-C_4)$alkyl, halo$(C_1-C_4)$alkyl or $(C_1-C_4)$alkoxy and aryl;
d is an integer selected from 0 or 1; and,
when d is 1,
J is selected from O, CH=CH, S(O)$_g$, HC=N, C(=O), OC(=O), C(=O)O, C(=O)NH, $NR^{19}$, N(oxide)$R^{19}$ and $NR^{19}$C(=O) where g and $R^{19}$ are as previously described;
X is selected from a substituted aryl or a substituted heteroaryl, wherein the substituents are independently selected from hydrogen, halogen, $(C_1-C_6)$alkyl, $(C_2-C_4)$alkenyl, $(C_2-C_4)$alkynyl, halo$(C_1-C_6)$alkyl, halo$(C_1-C_6)$alkoxy, hydroxy$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy$(C_{-C6})$alkyl, $(C_2-C_4)$alkenyloxy, $(C_2-C_4)$alkynyloxy, halo$(C_1-C_6)$alkoxy, halo$(C_2-C_4)$alkenyloxy, halo$(C_2-C_4)$alkynyloxy, $(C_1-C_6)$alkylthio, pentahalothio, $(C_1-C_6)$alkylsulfinyl, $(C_1-C_6)$alkylsulfonyl, halo$(C_1-C_6)$alkylthio, halo$(C_1-C_6)$alkylsulfinyl, halo$(C_1-C_6)$alkylsulfonyl, cyano, nitro; $NR^cR^d$, where $R^c$ and $R^d$ are independently selected from hydrogen, $(C_1-C_6)$alkyl, halo$(C_1-C_6)$alkyl, $(C_1-C_6)$alkylcarbonyl, and $(C_1-C_6)$alkoxycarbonyl, and where $R^c$ and $R^d$ may be taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$alkylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy;
provided that when X is a substituted aryl having the following structure,

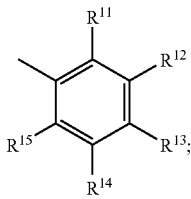

$R^{11}$ and $R^{12}$, or $R^{12}$ and $R^{13}$, or $R^{13}$ and $R^{14}$ or $R^{14}$ and $R^{15}$ are taken together with —$CR^{24}$=$CR^{25}CR^{26}$=$CR^{27}$—, —$OCR^{24}R^{25}CH_2$—, —$CH_2CR^{24}R^{25}O$—, —$OCR^{24}R^{25}O$—, —$OCR^{24}R^{25}CR^{26}R^{27}O$—, —$OCR^{24}R^{25}CH$=$CH$—, —$OCR^{24}R^{25}CH_2CH_2$—, —$OCR^{24}$=$N$—, —$N$=$CR^{24}O$—, —$ON$=$CR^{24}$—, —$ONR^{24}C$(=$O$)—, —$CH_2NR^{24}C$(=$O$)—, —$C_3H_6$—, —$C_2H_4$(C=O)—, —$SCR^{24}$=$N$—, —$OCR^{24}R^{25}C$(=$O$)—, —$CR^{24}$=$CR^{24}NR^{26}$—, —$CR^{24}$=$NNR^{25}$—, —$N$=$NNR^{24}$— or —$N$=$CR^{24}N$=$N$— to form a fused ring, where $R^{24}$ through $R^{27}$, inclusively, are independently selected from hydrogen, halogen, $(C_1$-$C_3)$alkyl, halo$(C_1$-$C_3)$alkyl, halo$(C_1$-$C_3)$alkoxy and aryl;

and agriculturally-acceptable salts thereof.

The present invention also includes compositions containing an insecticidally effective amount of at least one compound of formula I, and optionally, an effective amount of at least one second compound, with at least one insecticidally compatible carrier.

The present invention also includes methods of controlling insects, in an area where control is desired, which comprise applying an insecticidally effective amount of the above composition to the locus of crops, or other areas where insects are present or are expected to be present.

The present invention also includes novel intermediates finding utility in the syntheses of compounds of formula I.

DETAILED DESCRIPTION OF THE INVENTION

The present invention relates to certain new and useful insecticidal and acaricidal compounds, namely substituted cyclic urea derivatives (hereinafter termed "compounds of formula I") as depicted in general formula I:

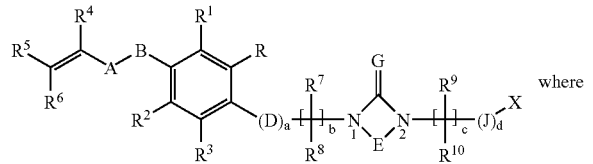

I

R and $R^3$ are independently selected from hydrogen, halogen, hydroxy, $(C_1$-$C_6)$alkyl, $(C_3$-$C_6)$cycloalkyl, $(C_2$-$C_5)$alkenyl, $(C_2$-$C_5)$alkynyl, halo$(C_1$-$C_3)$alkyl, $(C_1$-$C_3)$alkoxy, halo$(C_1$-$C_3)$alkoxy, $(C_1$-$C_3)$alkylthio, halo$(C_1$-$C_3)$alkylthio, $(C_1$-$C_3)$alkylsulfonyl, halo$(C_1$-$C_3)$alkylsulfonyl, cyano, nitro; optionally substituted amino wherein the optional substituent is selected from $(C_1$-$C_4)$alkyl, $(C_1$-$C_3)$alkylcarbonyl and $(C_1$-$C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —$C$(=$K$)-$L$, and —$C(R^{16})$-$M$-$R^{17}$, wherein the optional substituent is selected from $(C_1$-$C_4)$alkyl, halogen, halo$(C_1$-$C_4)$alkyl, $(C_1$-$C_4)$alkoxy, $(C_1$-$C_4)$alkoxy$(C_1$-$C_4)$alkyl, $(C_3$-$C_6)$cycloalkyl, $(C_2$-$C_5)$alkenyl, $(C_2$-$C_5)$alkynyl, cyano, nitro and aryl;

where

K is selected from O, S, $NR^{18}$, and $NOR^{18}$, where $R^{18}$ is hydrogen, $(C_1$-$C_4)$alkyl, halo$(C_1$-$C_4)$alkyl, aryl and aryl $(C_1$-$C_4)$alkyl;

L is selected from hydrogen, $(C_1$-$C_3)$alkyl, halo$(C_1$-$C_3)$alkyl, $(C_1$-$C_3)$alkoxy, $(C_1$-$C_3)$alkylamino and di$(C_1$-$C_3)$alkylamino;

M is selected from O, S, and $NR^{18}$, where $R^{18}$ is as previously described;

$R^{16}$ and $R^{17}$ are independently selected from hydrogen, $(C_1$-$C_4)$alkyl and halo$(C_1$-$C_4)$alkyl, and $R^{16}$ and $R^{17}$ may be taken together with -$Q(CHR^{18})_e$—, where e is an integer of 2 to 4; Q is selected from O, S, and $NR^{18}$, where $R^{18}$ is as previously described;

$R^1$ and $R^2$ are independently selected from hydrogen, halogen and $(C_1$-$C_3)$alkyl;

A is selected from O, S, *$OCH_2$ and $(CH_2)_f$ where the asterisk denotes attachment to B, and f is an integer selected from 1, 2 and 3;

B is selected from selected from $CH_2$, O, S and $NR^{19}$ where $R^{19}$ is selected from hydrogen, $(C_1$-$C_3)$alkyl, $(C_1$-$C_3)$alkoxy$(C_1$-$C_3)$alkyl, aryl$(C_1$-$C_3)$alkyl, $(C_2$-$C_4)$alkenyl $(C_1$-$C_3)$alkyl, halo$(C_2$-$C_4)$alkenyl$(C_1$-$C_3)$alkyl, di$(C_1$-$C_3)$alkylphosphonate, $(C_1$-$C_3)$alkylcarbonyl, halo$(C_1$-$C_3)$alkylcarbonyl, $(C_1$-$C_3)$alkoxy$(C_1$-$C_3)$alkylcarbonyl, arylcarbonyl and $(C_1$-$C_3)$alkylsulfonyl; provided that A and B are not simultaneously O or S;

$R^4$ is hydrogen;

$R^5$ and $R^6$ are independently selected from halogen;

a is an integer selected from 0 or 1;

and when a is 1,

D is O, $CH_2$, $OCH_2$, $CH_2O$, $OCH$=$CH$, $C$(=$O$), $S(O)_g$, —$CH$=$CH$—, —$OC$(=$O$)—, —$OC$(=$O$)$NH$—, —$NHC$(=$O$)—, —$NHSO_2$—, —$N$=$CH$—, $NR^{19}$, or N(oxide)$R^{19}$ where $R^{19}$ is as previously described, and g is an integer selected from 0, 1 or 2;

b is an integer selected from 0, 1, 2, 3, 4, 5 or 6;

and when b is 1 or more, $R^7$ and $R^8$ are independently selected from hydrogen, halogen, $(C_1$-$C_4)$alkyl, cyclo$(C_3$-$C_6)$alkyl, halo$(C_1$-$C_4)$alkyl and aryl;

E is a bridging group selected from —$CR^{20}$=$CR^{21}$—, *—$CR^{20}$=$N$—, *—$N$=$CR^{20}$—, —$N$=$N$—, *—$C$(=$O$) $CR^{20}R^{21}$—, *—$CR^{20}R^{21}C$(=$O$)—, —$(CR^{20}R^{21})_n$—, *—$N$=$CR^{20}C$(=$O$)—, *—$C$(=$O$)$CR^{20}$=$N$—, *—$C$(=$O$)$NR^{20}$—, *—$NR^{20}C$(=$O$)—, *—$CR^{20}$=$CR^{21}C$(=$O$)—, *—$C$(=$O$)$CR^{21}$=$CR^{20}$—, —$CR^{20}R^{21}OCR^{22}R^{23}$—, —$C$(=$O$)$C$(=$O$)—, *—$S(O)_gCR^{20}R^{21}$—, *—$S(O)_gNR^{20}$—, *—$OCR^{22}R^{23}$—, *—$CR^{22}R^{23}O$— and —$C$(=$O$)— where the asterisk denotes attachment at the position designated as 1 in formula I, g is as previously described, n is an integer selected from 2, 3, and 4, and $R^{20}$ through $R^{23}$, inclusively, are independently selected from hydrogen, halogen, $(C_1$-$C_4)$alkyl, $(C_1$-$C_4)$alkoxy, $(C_1$-$C_4)$alkoxy$(C_1$-$C_4)$alkyl, halo$(C_1$-$C_4)$alkyl, $(C_1$-$C_4)$alkoxycarbonyl, nitro, cyano, amino, $(C_1$-$C_4)$alkylamino and aryl; and $R^{20}$ through $R^{23}$ in geminal positions may be taken together to form 5-, 6- or 7-membered spiro rings comprised of carbon, nitrogen and oxygen, or $R^{20}$ through $R^{23}$ in adjacent positions may be taken together to form 5-, 6- or 7-membered rings comprised of carbon, nitrogen and oxygen or a benzo-fused ring;

G is selected from O, S, N-Q, or C-Q, where Q is cyano or nitro;

c is an integer selected from 0, 1, 2, 3 or 4;
and when c is 1 or more, $R^9$ and $R^{10}$ are independently selected from hydrogen, $(C_1-C_4)$alkyl, halo$(C_1-C_4)$alkyl or $(C_1-C_4)$alkoxy and aryl;

d is an integer selected from 0 or 1; and, when d is 1,

J is selected from O, CH=CH, S(O)$_g$, HC=N, C(=O), OC(=O), C(=O)O, C(=O)NH, $NR^{19}$, N(oxide)$R^{19}$ and $NR^{19}C$(=O) where g and $R^{19}$ are as previously described;

X is selected from a substituted aryl or a substituted heteroaryl, wherein the substituents are independently selected from hydrogen, halogen, $(C_1-C_6)$alkyl, $(C_2-C_4)$alkenyl, $(C_2-C_4)$alkynyl, halo$(C_1-C_6)$alkyl, halo$(C_1-C_6)$alkoxy, hydroxy$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy$(C_1-C_6)$alkyl, $(C_2-C_4)$alkenyloxy, $(C_2-C_4)$alkynyloxy, halo$(C_1-C_6)$alkoxy, halo$(C_2-C_4)$alkenyloxy, halo$(C_2-C_4)$alkynyloxy, $(C_1-C_6)$alkylthio, pentahalothio, $(C_1-C_6)$alkylsulfinyl, $(C_1-C_6)$alkylsulfonyl, halo$(C_1-C_6)$alkylthio, halo$(C_1-C_6)$alkylsulfinyl, halo$(C_1-C_6)$alkylsulfonyl, cyano, nitro; $NR^cR^d$, where $R^c$ and $R^d$ are independently selected from hydrogen, $(C_1-C_6)$alkyl, halo$(C_1-C_6)$alkyl, $(C_1-C_6)$alkylcarbonyl, and $(C_1-C_6)$alkoxycarbonyl, and where $R^c$ and $R^d$ may be taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$alkylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy;

provided that when X is a substituted aryl having the following structure,

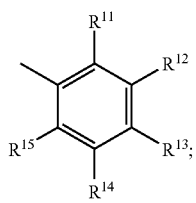

$R^{11}$ and $R^{12}$, or $R^{12}$ and $R^{13}$, or $R^{13}$ and $R^{14}$ or $R^{14}$ and $R^{15}$ are taken together with —CR$^{24}$=CR$^{25}$CR$^{26}$=CR$^{27}$—, —OCR$^{24}$R$^{25}$CH$_2$—, —CH$_2$CR$^{24}$R$^{25}$O—, —OCR$^{24}$R$^{25}$O—, —OCR$^{24}$R$^{25}$CR$^{26}$R$^{27}$O—, —OCR$^{24}$R$^{25}$CH=CH—, —OCR$^{24}$R$^{25}$CH$_2$CH$_2$—, —OCR$^{24}$=N—, —N=CR$^{24}$O—, —ON=CR$^{24}$, —ONR$^{24}$C(=O)—, —CH$_2$NR$^{24}$C(=O)—, —C$_3$H$_6$—, —C$_2$H$_4$(C=O)—, —SCR$^{24}$=N—, —OCR$^{24}$R$^{25}$C(=O)—, —CR$^{24}$=CR$^{25}$NR$^{26}$—, —CR$^{24}$=NNR$^{25}$—, —N=NNR$^{24}$— or —N=CR$^{24}$N=N— to form a fused ring, where $R^{24}$ through $R^{27}$, inclusively, are independently selected from hydrogen, halogen, $(C_1-C_3)$alkyl, halo$(C_1-C_3)$alkyl, halo$(C_1-C_3)$alkoxy and aryl;

and
agriculturally-acceptable salts thereof.

Preferred substituted cyclic urea derivatives from the group set forth above are those compounds of Formula I where:

R and $R^3$ are independently selected from halogen and $(C_1-C_3)$alkyl;

A is $(CH_2)f$ where f is 1; B is O;

$R^5$ and $R^6$ are independently selected from chlorine and bromine;

a is an integer selected from 0 or 1, and when a is 1, D is selected from O, CH$_2$ and OCH$_2$;

b is an integer selected from 0, 1, 2, 3, 4, 5 or 6, and when b is 1 or more, $R^7$ and $R^8$ are each hydrogen;

E is said bridging group selected from —CR$^{20}$=CR$^{21}$—, *—CR$^{20}$=N—, *—N=CR$^{20}$— and —N=N—, where $R^{20}$ and $R^{21}$ are independently selected from hydrogen and $(C_1-C_4)$alkyl;

G is selected from O or S;

c is an integer selected from 0, 1, 2, 3 and 4, and when c is 1 or more, $R^9$ and $R^{10}$ are each hydrogen;

d is an integer selected from 0 or 1, and when d is 1, J is selected from O, C(=O) and S(O)$_g$ where g is 2;

X is a substituted aryl or substituted heteroaryl wherein the substituents are independently selected from hydrogen, halogen, $(C_1-C_6)$alkyl, halo$(C_1-C_3)$alkyl, halo$(C_1-C_3)$alkoxy and halo$(C_1-C_6)$alkylsulfonyl; provided that when X is a substituted aryl having the following structure,

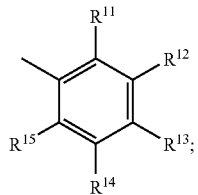

$R^{11}$ and $R^{12}$ or $R^{13}$ and $R^{14}$ may be taken together with —OCR$^{24}$R$^{25}$CH$_2$—, —CH$_2$CR$^{24}$R$^{25}$O—, —CR$^{24}$=CR$^{25}$CR$^{26}$=CR$^{27}$—, —OCR$^{24}$R$^{25}$O— or —OCR$^{24}$=N— to form a fused ring, where $R^{24}$, $R^{25}$, $R^{26}$ and $R^{27}$ are each hydrogen, chlorine, fluorine, $(C_1-C_3)$alkyl, halo$(C_1-C_3)$alkyl or halo$(C_1-C_3)$alkoxy.

More preferred substituted cyclic urea derivatives of the group set forth above are those where R and $R^3$ are each chlorine; $R^1$ and $R^2$ are each hydrogen; a is 1 and D is 0; b is an integer selected from 2, 3 or 4; E is a bridging group selected from —CR$^{20}$=N—, —N=CR$^{20}$— or —N=N—, where $R^{20}$ is selected from hydrogen or methyl; G is O; c is an integer selected from 0 or 1; d is 0; and X is a substituted aryl have the following structure,

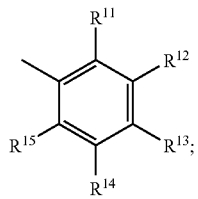

where $R^{11}$ through $R^{15}$, inclusively, are independently selected from hydrogen, halogen, $(C_1-C_6)$alkyl, halo$(C_1-C_3)$alkyl, halo$(C_1-C_3)$alkoxy and halo$(C_1-C_6)$alkylsulfonyl, and where $R^{11}$ and $R^{12}$ may be taken together with —OCR$^{24}$R$^{25}$CH$_2$—, —OCR$^{24}$R$^{25}$O— or —OCR$^{24}$=N— to form a fused ring, where R$^{24}$ and R$^{25}$ are selected from (C$_1$-C$_3$)alkyl and halo(C$_1$-C$_3$)alkyl.

Yet more preferred phenylalkyl substituted cyclic urea derivatives are those where R$^{11}$ through R$^{15}$, inclusively, are independently selected from hydrogen, chlorine, fluorine, 1,1-dimethylethyl, trifluoromethyl, and difluoromethylsulfonyl; and where R$^{11}$ and R$^{12}$ may be taken together with —OCR$^{24}$R$^{25}$CH$_2$—, —OCR$^{24}$R$^{25}$O— or —OCR$^{24}$=N— to form a fused ring, where R$^{24}$ and R$^{25}$ are each methyl or trifluoromethyl.

Yet more preferred phenylalkyl substituted cyclic urea derivatives are those where R$^{11}$ through R$^{15}$, inclusively, are independently selected from halogen or halo(C$_1$-C$_3$)alkyl; E is —N=N— and b is 4.

Another embodiment of the present invention is a compound of formula I-JJ

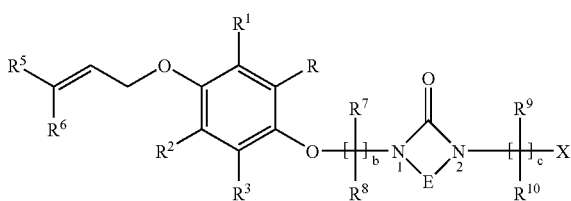

I-JJ where

R and R$^3$ are independently selected from halogen and hydroxy;

R$^1$ and R$^2$ are independently selected from hydrogen, halogen and (C$_1$-C$_3$)alkyl;

R$^5$ and R are independently selected from halogen;

b is an integer selected from 2, 3 or 4;

R$^7$ and R$^8$ are independently selected from hydrogen, halogen, (C$_1$-C$_4$)alkyl, and halo(C$_1$-C$_4$)alkyl;

E is a bridging group selected from *—CR$^{20}$=N—, *—N=CR$^{20}$— and —N=N— where the asterisk denotes attachment at the position designated as 1 in formula I-JJ, and R$^{20}$ is selected from hydrogen, halogen, (C$_1$-C$_4$)alkyl, (C$_1$-C$_4$)alkoxy, (C$_1$-C$_4$)alkoxy(C$_1$-C$_4$)alkyl and halo(C$_1$-C$_4$)alkyl;

c is an integer selected from 0, 1, 2, 3 or 4;

and when c is 1 or more,

R$^9$ and R$^{10}$ are independently selected from hydrogen, (C$_1$-C$_4$)alkyl, halo(C$_1$-C$_4$)alkyl and (C$_1$-C$_4$)alkoxy;

X is selected from a substituted aryl or a substituted heteroaryl, wherein the substituents are independently selected from hydrogen, halogen, (C$_1$-C$_6$)alkyl, halo(C$_1$-C$_6$)alkyl and halo(C$_1$-C$_6$)alkoxy;

and agriculturally-acceptable salts thereof.

Yet another embodiment of the present invention is a compound of formula I-KK

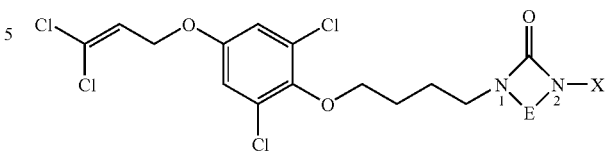

I-KK where

E is a bridging group selected from *—CH=N—, *—N=CH— and —N=N— where the asterisk denotes attachment at the position designated as 1 in formula I-KK;

X is selected from a substituted aryl wherein the substituents are independently selected from hydrogen, halogen, (C$_1$-C$_6$)alkyl, halo(C$_1$-C$_6$)alkyl and halo(C$_1$-C$_6$)alkoxy;

and agriculturally-acceptable salts thereof.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention comprise causing an insecticidally effective amount of a compound of formula I to be administered to insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which are referred to as pro-insecticides.

Another aspect of the present invention relates to compositions containing an insecticidally effective amount of at least one compound of formula I.

Another aspect of the present invention relates to compositions containing an insecticidally effective amount of at least one compound of formula I, and an effective amount of at least one second compound.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

Another aspect of the present invention relates to novel intermediates finding utility in the syntheses of compounds of formula I.

The present invention also includes the use of the compounds and compositions set forth herein for control of non-agricultural insect species, for example, dry wood termites and subterranean termites; as well as for use as pharmaceutical agents. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure having up to six carbon atoms, for example, phenyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of; while the term "TLC analysis" refers to thin layer chromatographic analysis of, for example a reaction mixture. The term "HPLC" refers to high pressure liquid chromatography, as it relates to, for example a method of separating components from a reaction mixture. The term "DMF" refers to N,N-dimethylformamide. The term "THF" refers to tetrahydrofuran. The term "DBU" refers to 1,8-diazabicyclo[5.4.0]undec-7-ene. The term "DEAD" refers to diethyl azodicarboxylate. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids. The term "independently selected from" as set forth above and in the claims section of the present specification refers to the possibility that moieties, for example the $R^5$ and $R^6$, may be the same or they may be different within the group that the selection is made.

The phenylalkyl substituted cyclic urea derivatives of formula I can be synthesized by methods that are individually known to one skilled in the art from available intermediate compounds.

Scheme 1 below illustrates a general procedure for synthesizing phenylalkyl substituted cyclic urea derivatives of formula I, inter alia, where, for example, $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; b is 4; E is —$CR^{20}$=N—; c and d are 0; X is a substituted aryl:

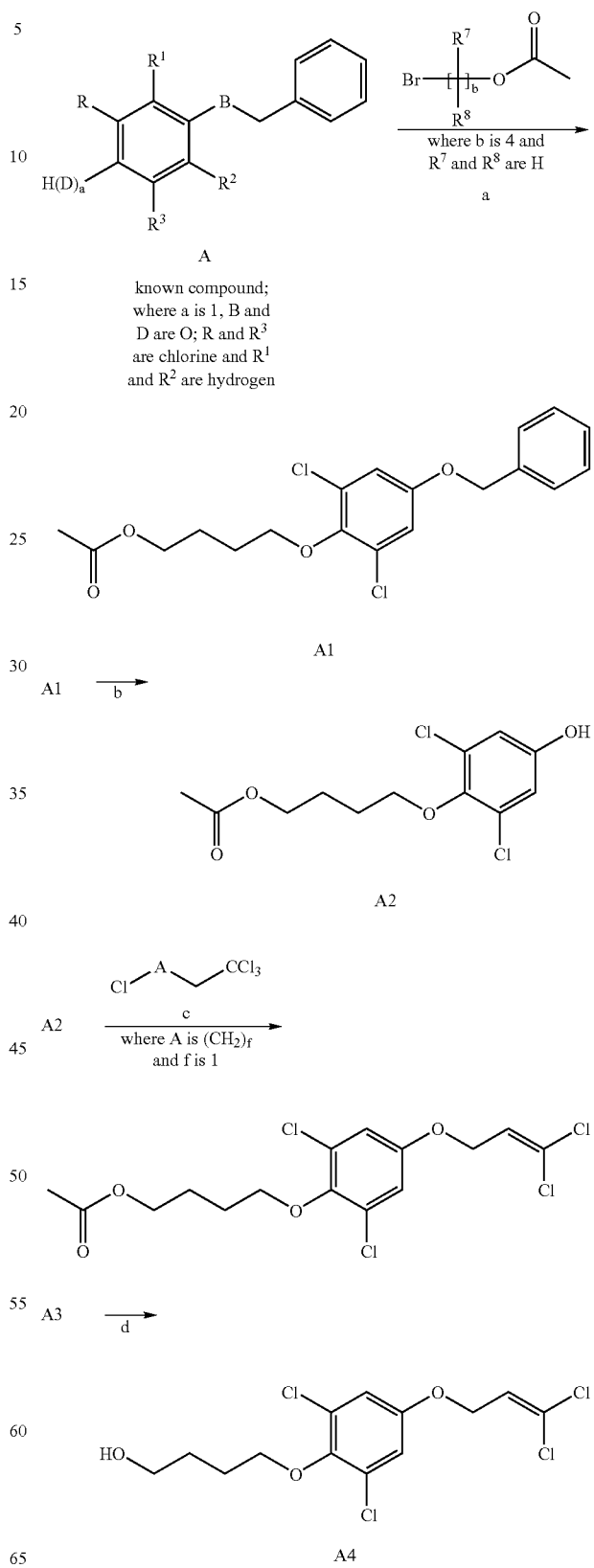

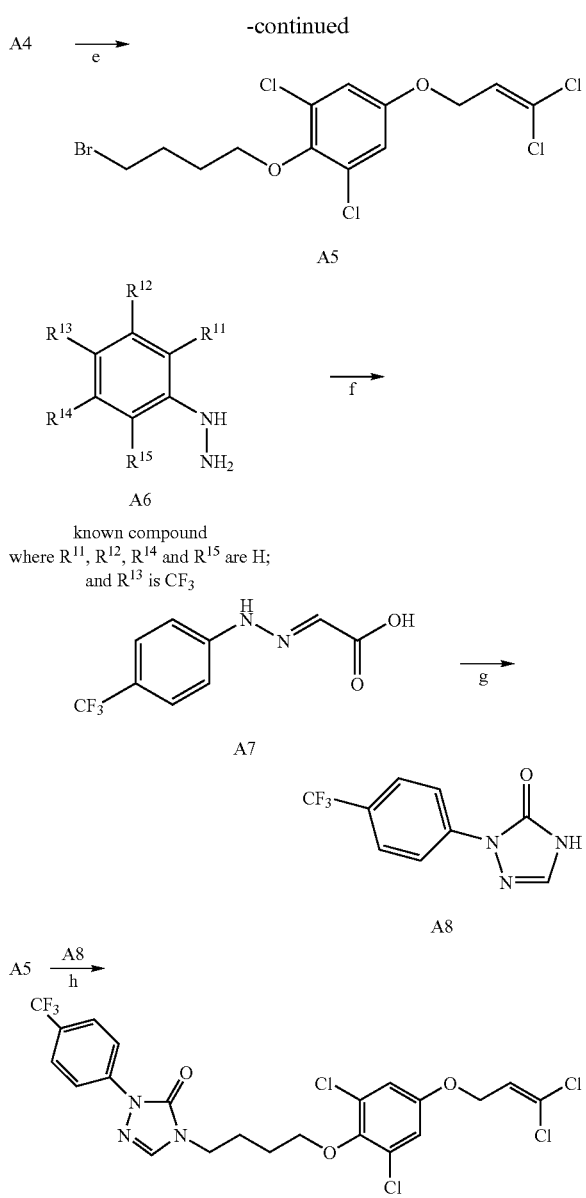

A5

A6
known compound
where R$^{11}$, R$^{12}$, R$^{14}$ and R$^{15}$ are H;
and R$^{13}$ is CF$_3$

A7

A8 compound of formula I
a) K$_2$CO$_3$/DMF/80° C.  b) H$_2$10% Pd on carbon/EtOH  c) K$_2$CO$_3$/DMF/80° C.
d) NaOH/MeOH  e) CBr$_4$/Ph$_3$P/CH$_2$Cl$_2$  f) glyoxylic acid/HCl/H$_2$O/RT
g) Diphenylphosphoryl azide/Et$_3$N/Toluene/reflux  h) K$_2$CO$_3$/DMF/80° C.

As depicted in scheme 1 in a first series of reactions, the known compound 2,6-dichloro-4-phenylmethoxyphenol was reacted under basic conditions with, for example a haloalkyl ester such as of 4-bromobutyl acetate, affording the corresponding ester (A1), for example 4-[2,6-dichloro-4-(phenylmethoxy)phenoxy]butyl acetate. Intermediate (A1) was in turn deprotected by treating it with hydrogen gas under catalytic hydrogenation conditions, providing intermediate (A2). Intermediate (A2) was then treated with, for example 1,1,1,3-tetrachloropropane, under basic conditions, affording the corresponding intermediate (A3), which was in turn reduced with strong base, providing an alcohol intermediate (A4), for example 4-[4-(3,3-dichloro-2-propenyloxy)-2,6-dichlorophenoxy]butan-1-ol. Intermediate (A4) was brominated providing the corresponding 1-[4-(3,3-dichloroprop-2-enyloxy)-2,6-dichlorophenoxy]-4-bromobutane (A5)

In a second series of reactions, the known compound 4-trifluoromethylphenylhydrazine (A6) was reacted with, for example glyoxylic acid under acidic conditions, yielding the corresponding aminopropenoic acid (A7), which was in turn cyclized with diphenylphosphoryl azide under basic conditions, affording the corresponding 1-substituted-1,2,4-triazolin-5-one (A8) as an intermediate. Intermediates (A5) and (A8) were then reacted under basic conditions, providing compounds of formula I, such as 4-{4-[4-(3,3-Dichloroprop-2-enyloxy)-2,6-dichlorophenoxy]butyl}-1-[4-(trifluoromethyl)phenyl]-1,2,4-triazolin-5-one.

Scheme 2 below illustrates a general procedure for synthesizing phenylalkyl substituted cyclic urea derivatives of formula I, inter alia, where, for example, R$^1$, R$^2$, R$^4$ R$^7$, R$^8$ are hydrogen; R, R$^3$, R$^5$ and R$^6$ are chlorine; A is (CH$_2$)$_f$ where f is 1; B and G are O, a is 1, and D is O; b is 4; E is —N=N—; c and d are 0; X is a substituted aryl:

Scheme 2:

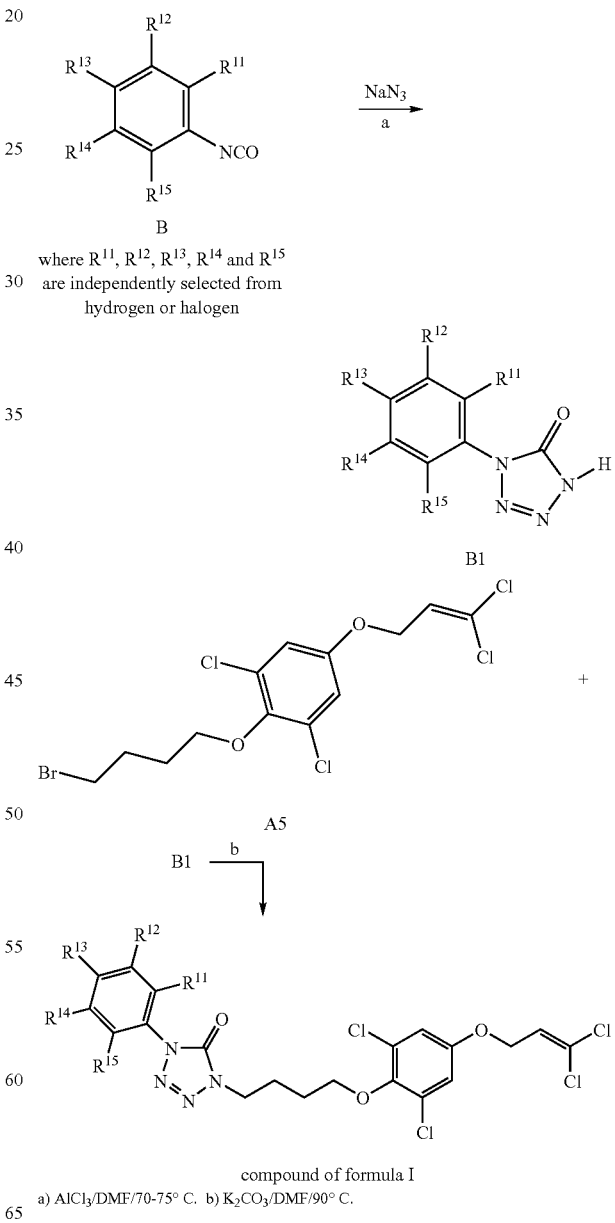

B
where R$^{11}$, R$^{12}$, R$^{13}$, R$^{14}$ and R$^{15}$ are independently selected from hydrogen or halogen

B1

A5 compound of formula I
a) AlCl$_3$/DMF/70-75° C.  b) K$_2$CO$_3$/DMF/90° C.

As depicted in scheme 2, a substituted phenylisocyanate (B), for example the known compound 3-chlorophenylisocyanate, was reacted with sodium azide in the presence of aluminum chloride to afford a 1-(3-halophenyl)-tetrazoline-5-one (B1), for example 1-(3-chlorophenyl)-tetrazolin-5-one. Intermediate (B1) and Intermediate (A5), prepared in scheme 1 above, were then reacted under basic conditions, providing compounds of formula I, such as 1-{4-[4-(3,3-dichloroprop-2-enyloxy)-2,6-dichlorophenoxy]butyl}-4-(3-chlorophenyl)-1,2,3,4-tetrazolin-5-one.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfon-amide ("achlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]amino]sulfonyl]-1-methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]-propanoic acid (fenoxaprop"), (+/−)-2-[4[[5-(trifluoromethyl)-2-pyridinyl]oxy]-phenoxy] propanoic acid ("fluazifop"), (+/−)-2-[4-(6chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid and non-pyrethroid insecticides, such as fenvalerate, deltamethrin, fenpropathrin, cyfluthrin, flucythrinate, alpha-cypermethrin, bifenthrin, cypermethrin, resolved cyhalothrin, etofenprox, esfenvalerate, tralomethrin, tefluthrin, cycloprothrin, betacyfluthrin, acrinathrin and silafluofen; carbamate insecticides, such as aldicarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, noviflumuron, flufenoxuron, and lufenuron; and other insecticides, such as, without limitation, amitraz, clofentezine, fenpyroximate, hexythiazox, cyhexatin, spinosad, imidacloprid, chlorfenaptr, hydramethylon, acequinocyl, fenbutatin-oxide, methoxyfenozide, tebufenozide, halofenozide, indoxacarb, fipronyl, ethiprole, etoxazole, bifenazate, spirodiclofen, spiromesifen, methoprene, pyriproxyfen, fenoxycarb, pymetrozine, abamectin, emamectin benzoate, milbemectin, and other insecticides.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldicarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of 4-{4-[4-(3,3-Dichloroprop-2-enyloxy)-2,6-dichlorophenoxy]butyl}-1-[4-(trifluoromethyl)-phenyl]-1,2,4-triazolin-5-one (Compound 107 in table below)

Step A Synthesis of 4-[2,6-dichloro-4-(phenylmethoxy)phenoxy]butyl acetate as an Intermediate Under a nitrogen atmosphere, a solution of 25 grams (0.093 mole) of 2,6-dichloro-4-phenylmethoxyphenol (known compound), 19.5 grams (0.10 mole) of 4-bromobutyl acetate and 19.4 grams (0.14 mole) of potassium carbonate in 400 mL of DMF was stirred at ambient temperature for two hours, then it was heated to 80° C. where it was maintained during a 20 hour period. After this time the reaction mixture was allowed to cool to ambient temperature where it stirred during an additional 20 hour period. The reaction mixture was then stirred with 400 mL of water, saturated with sodium chloride and extracted with four 150 mL portions of diethyl ether. The combined extracts were washed with two 150 mL portions of water, dried with sodium sulfate and filtered. The filtrate was concentrated under reduced pressure to a residue. The crude residue was purified with column chromatography on silica gel using 1:1 methylene chloride:hexane as an eluant. The appropriate fractions were combined and concentrated under reduced pressure, yielding 33.1 grams of compound the subject compound. The NMR spectrum was consistent with the proposed structure.

Step B Synthesis of 4-(2,6-dichloro-4-hydroxyphenoxy)butyl acetate as an Intermediate A mixture of 33.0 grams (0.086 mole) of 4-[2,6-dichloro-4-(phenylmethoxy)phenoxy]butyl acetate and 0.05 gram (catalyst) of 10% palladium on carbon in 350 mL of ethanol was subjected to hydrogenation conditions using a Parr hydrogenator. After the theoretical uptake of hydrogen, gas chromatographic (GC) analysis of the reaction mixture indicated the reaction was about 50% complete. Additional catalyst was added and the reaction mixture was again subjected to hydrogenation conditions using the Parr hydrogenator. GC analysis of the reaction mixture indicated the reaction was now complete. The reaction mixture was filtered and concentrated under reduced pressure, yielding 25.4 grams of the subject compound as a residue. The NMR spectrum was consistent with the proposed structure.

Step C Synthesis of 4-[4-(3,3-dichloroprop-2-enyloxy)-2,6-dichlorophenoxy]butyl acetate as an Intermediate A solution of 25.3 grams (0.086 mole) of 4-(2,6-dichloro-4-hydroxyphenoxy)butyl acetate in 250 mL of DMF was stirred, and 19.5 grams (0.1 mole) of 1,1,1,3-tetrachloropropane was added, followed by 18 grams (0.13 mole) of potassium carbonate. Upon completion of addition the reaction mixture was heated at 80° C. during a 17 hour period. After this time the reaction mixture was cooled to ambient temperature, stirred with 350 mL of water and extracted with four 150 mL portions of diethyl ether. The combined extracts were washed with two 100 mL portions of water, dried with sodium sulfate and filtered. The filtrate was concentrated under reduced pressure to a residue. The residue was purified with column chromatography on silica gel using 1:1 methylene chloride:hexane as an eluant. The appropriate fractions were combined and concentrated under reduced pressure, yielding 27.1 grams of the subject compound. The NMR spectrum was consistent with the proposed structure.

Step D Synthesis of 4-[4-(3,3-dichloro-2-propenyloxy)-2,6-dichlorophenoxy]butan-1-ol as an Intermediate Twenty seven grams (0.067 mole) of 4-[4-(3,3-dichloroprop-2-enyloxy)-2,6-dichlorophenoxy]butyl acetate was stirred and a solution of 5.4 grams (0.134 mole) of sodium hydroxide in 300 mL of methanol was added portion-wise. Upon completion of addition the reaction mixture was stirred at ambient temperature during a two hour period. After this time the reaction mixture was stirred with 400 mL of water and was neutralized with concentrated hydrochloric acid. The neutral mixture was extracted with four 150 mL portions of diethyl ether, and the combined extracted were washed with one 150 mL portion of an aqueous solution saturated with sodium chloride. The organic layer was dried with sodium sulfate, filtered, and the filtrate was concentrated under reduced pressure to a residue, yielding 22.5 grams of the subject compound. The NMR spectrum was consistent with the proposed structure.

Step E Synthesis of 1-[4-(3,3-dichloroprop-2-enyloxy)-2,6-dichlorophenoxy]-4-bromobutane as an Intermediate A stirred solution of 22.3 grams (0.062 mole) of 4-[4-(3,3-dichloro-2-propenyloxy)-2,6-dichlorophenoxy]butan-1-ol and 20.6 grams (0.062 mole) of carbon tetrabromide in 250 mL of methylene chloride was cooled to 10° C. and 17.9 grams (0.068 mole) of triphenylphosphine was added in one portion. Upon completion of addition the reaction mixture was warmed to ambient temperature where it stirred during an 18 hour period. After this time the reaction mixture was concentrated under reduced pressure to a residue. The residue was purified with column chromatography on silica gel using 25% methylene chloride in hexane as an eluant. The appropriate fractions were combined and concentrated under reduced pressure, yielding 21.3 grams of the subject compound. The NMR spectrum was consistent with the proposed structure.

Step F Synthesis of (2E)-3-aza-3-{[4-(trifluoromethyl)phenyl]amino}prop-2-enoic acid as an intermediate A suspension of 1.0 gram (0.006 mole) of 4-trifluoromethylphenylhydrazine (known compound) in 10 mL of water was stirred and 0.4 mL (0.007 mole) of glyoxylic acid was added, followed by a solution of 1 mL of concentrated hydrochloric acid in 2 mL of water. Upon completion of addition the reaction mixture was stirred at ambient temperature during a one hour period. After this time the reaction mixture was filtered to collect, when dried, 0.6 gram of the subject compound as a solid. The NMR spectrum was consistent with the proposed structure.

Step G Synthesis of 1-[4-(trifluoromethyl)phenyl]-1,2,4-triazolin-5-one as an intermediate A suspension of 0.6 gram (0.0024 mole) of (2E)-3-aza-3-{[4-(trifluoromethyl)phenyl]amino}prop-2-enoic acid in 15 mL of toluene was stirred and 0.34 mL (0.0024 mole) of triethylamine, followed by 0.53 mL (0.0024 mole) of diphenylphosphoryl azide were added, each in one portion. Upon completion of addition the reaction mixture was slowly warmed to reflux temperature where it was maintained for one hour. After this time the reaction mixture was poured into 100 mL of an aqueous 10% potassium hydroxide solution. The aqueous basic layer was separated, cooled in an ice-water bath and acidified with concentrated hydrochloric acid. The resultant solid precipitate was collected by filtration and dried, yielding 0.5 gram of the subject compound. The NMR spectrum was consistent with the proposed structure.

Step H Synthesis of Compound 107

A stirred solution of 0.20 gram (0.0005 mole) of 1-[4-(3,3-dichloroprop-2-enyloxy)-2,6-dichlorophenoxy]-4-bromobutane (prepared in Steps A-E of the present Example), 0.11 gram (0.0005 mole) of 1-[4-(trifluoromethyl)phenyl]-1,2,4-triazolin-5-one (prepared in Steps F and G of the present Example), 0.10 gram (0.0008 mole) of potassium carbonate and 0.10 gram (catalyst) of 18-Crown-6 in 10 mL of DMF was heated to 80° C. where it was maintained during an 18 hour period. After this time the reaction mixture was cooled to ambient temperature, diluted with 50 mL of distilled water and extracted with 200 mL of diethyl ether. The extract was then washed with 50 mL of distilled water, dried with sodium sulfate and filtered. The filtrate was concentrated under reduced pressure to a residue. The residue was purified with column chromatography on silica gel using methylene chloride as an eluant. The appropriate fractions were combined and concentrated under reduced pressure, yielding 0.08 grams of the subject compound. The NMR spectrum was consistent with the proposed structure.

EXAMPLE 2

This example illustrates one protocol for the preparation of 1-{4-[4-(3,3-dichloroprop-2-enyloxy)-2,6-dichlorophenoxy]butyl}-4-(3-chlorophenyl)-1,2,3,4-tetrazolin-5-one (Compound 310 in table below)

Step A Synthesis of 1-(3-chlorophenyl)-tetrazolin-5-one as an Intermediate

DMF (5.0 ml) was cooled to 0° C. and stirred as 0.48 gram (0.0074 mole) of sodium azide was added. To this mixture was added 50 milligrams of aluminum chloride. The mixture was heated to 70° C. for 15 minutes, then the known compound 3-chlorophenylisocyanate was added neet in one portion. The mixture was heated at 75° C. for 3 hours and then cooled and poured into 100 ml of water containing 0.5 gram of sodium nitrite and 50 grams ice. To this was slowly added sufficient 10% hydrogen chloride to cause a change in KI/starch test paper. The resulting solid was filtered and dried. The filtrate was dissolved in ethyl acetate, washed with water and concentrated to a residue. The crude residue was purified with column chromatography on silica gel using 95:5 dichloromethane-methanol as an eluant yielding 0.38 gram of 1-(3-chlorophenyl)-tetrazolin-5-one.

Step B Synthesis of Compound 310

A stirred solution of 0.54 gram (0.0013 mole) of 1-[4-(3,3-dichloroprop-2-enyloxy)-2,6-dichlorophenoxy]-4-bromobutane (prepared in Steps A-E of Example 1), 0.25 gram (0.0013 mole) of 1-(3-chlorophenyl)-tetrazolin-5-one (prepared in Step A of the present Example), 0.18 gram (0.0013 mole) of potassium carbonate and 3 mL of DMF was heated to 90° C. where it was maintained during a 1 hour period. After this time the reaction mixture was cooled to ambient temperature and poured into 50 mL of saturated aqueous ammonium chloride. The reaction mixture was extracted twice with 50 mL of ethyl acetate. The extract was then washed with saturated aqueous sodium chloride, dried over magnesium sulfate and filtered. The filtrate was concentrated under reduced pressure to a residue. The residue was purified with preparative TLC plates with 9:1 heptane-ethyl acetate as an eluant yielding 0.46 grams of the subject compound. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some compounds of formula I:

TABLE 1

Phenylalkyl Substituted Cyclic Urea Derivatives

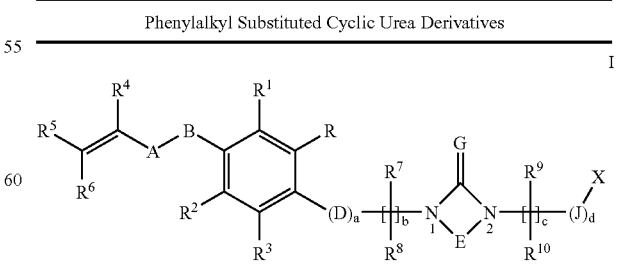

I

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=$CR^{21}$—; c and d are 0; X is aryl substituted with $R^{11}$ through $R^{15}$; providing the following compounds:

TABLE 1-continued

Phenylalkyl Substituted Cyclic Urea Derivatives

I-A

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$; providing the following compounds:

| Cmpd. No | b | $R^{20}$ | $R^{21}$ | $R^{11}$ | $R^{12}$ | $R^{13}$ | $R^{14}$ | $R^{15}$ |
|---|---|---|---|---|---|---|---|---|
| 1 | 4 | H | H | H | H | H | H | H |
| 2 | 4 | H | H | Cl | H | H | H | H |
| 3 | 4 | H | H | H | Cl | H | H | H |
| 4 | 4 | H | H | H | H | Cl | H | H |
| 5 | 4 | H | H | Cl | Cl | H | H | H |
| 6 | 4 | H | H | Cl | H | Cl | H | H |
| 7 | 4 | H | H | Cl | H | H | Cl | H |
| 8 | 4 | H | H | Cl | H | H | H | Cl |
| 9 | 4 | H | H | H | Cl | Cl | H | H |
| 10 | 4 | H | H | H | Cl | H | Cl | H |
| 11 | 4 | H | H | $CF_3$ | H | H | H | H |
| 12 | 4 | H | H | H | $CF_3$ | H | H | H |
| 13 | 4 | H | H | H | H | $CF_3$ | H | H |
| 14 | 4 | H | H | $OCF_3$ | H | H | H | H |
| 15 | 4 | H | H | H | $OCF_3$ | H | H | H |
| 16 | 4 | H | H | H | H | $OCF_3$ | H | H |
| 17 | 4 | H | H | $CH_3$ | H | H | H | H |
| 18 | 4 | H | H | H | $CH_3$ | H | H | H |
| 19 | 4 | H | H | H | H | $CH_3$ | H | H |
| 20 | 4 | H | H | $CH_3$ | $CH_3$ | H | H | H |
| 21 | 4 | H | H | $CH_3$ | H | $CH_3$ | H | H |
| 22 | 4 | H | H | $CH_3$ | H | H | $CH_3$ | H |
| 23 | 4 | H | H | $CH_3$ | H | H | H | $CH_3$ |
| 24 | 4 | H | H | H | $CH_3$ | $CH_3$ | H | H |
| 25 | 4 | H | H | H | $CH_3$ | H | $CH_3$ | H |
| 26 | 4 | H | H | F | H | H | H | H |
| 27 | 4 | H | H | H | F | H | H | H |
| 28 | 4 | H | H | H | H | F | H | H |
| 29 | 4 | H | H | F | F | H | H | H |
| 30 | 4 | H | H | F | H | F | H | H |
| 31 | 4 | H | H | F | H | H | F | H |
| 32 | 4 | H | H | F | H | H | H | F |
| 33 | 4 | H | H | H | F | F | H | H |
| 34 | 4 | H | H | H | F | H | F | H |
| 35 | 4 | H | H | Br | H | H | H | H |
| 36 | 4 | H | H | H | Br | H | H | H |
| 37 | 4 | H | H | H | H | Br | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —N=$CR^{20}$—; c and d are 0; X is aryl substituted with $R^{11}$ through $R^{15}$; providing the following compounds:

I-B

| Cmpd. No | b | $R^{20}$ | $R^{11}$ | $R^{12}$ | $R^{13}$ | $R^{14}$ | $R^{15}$ |
|---|---|---|---|---|---|---|---|
| 38 | 4 | H | H | H | H | H | H |
| 39 | 4 | H | Cl | H | H | H | H |
| 40 | 4 | H | H | Cl | H | H | H |
| 41 | 4 | H | H | H | Cl | H | H |
| 42 | 4 | H | Cl | Cl | H | H | H |
| 43 | 4 | H | Cl | H | Cl | H | H |
| 44 | 4 | H | Cl | H | H | Cl | H |
| 45 | 4 | H | Cl | H | H | H | Cl |
| 46 | 4 | H | H | Cl | Cl | H | H |
| 47 | 4 | H | H | Cl | H | Cl | H |
| 48 | 4 | H | $CF_3$ | H | H | H | H |
| 49 | 4 | H | H | $CF_3$ | H | H | H |
| 50 | 4 | H | H | H | $CF_3$ | H | H |
| 51 | 4 | H | $OCF_3$ | H | H | H | H |
| 52 | 4 | H | H | $OCF_3$ | H | H | H |
| 53 | 4 | H | H | H | $OCF_3$ | H | H |
| 54 | 4 | H | $CH_3$ | H | H | H | H |
| 55 | 4 | H | H | $CH_3$ | H | H | H |
| 56 | 4 | H | H | H | $CH_3$ | H | H |
| 57 | 4 | H | $CH_3$ | $CH_3$ | H | H | H |
| 58 | 4 | H | $CH_3$ | H | $CH_3$ | H | H |
| 59 | 4 | H | $CH_3$ | H | H | $CH_3$ | H |
| 60 | 4 | H | $CH_3$ | H | H | H | $CH_3$ |
| 61 | 4 | H | H | $CH_3$ | $CH_3$ | H | H |
| 62 | 4 | H | H | $CH_3$ | H | $CH_3$ | H |
| 63 | 4 | H | F | H | H | H | H |
| 64 | 4 | H | H | F | H | H | H |
| 65 | 4 | H | H | H | F | H | H |
| 66 | 4 | H | F | F | H | H | H |
| 67 | 4 | H | F | H | F | H | H |
| 68 | 4 | H | F | H | H | F | H |
| 69 | 4 | H | F | H | H | H | F |
| 70 | 4 | H | H | F | F | H | H |
| 71 | 4 | H | H | F | H | F | H |
| 72 | 4 | H | Br | H | H | H | H |
| 73 | 4 | H | H | Br | H | H | H |
| 74 | 4 | H | H | H | Br | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$; providing the following compounds:

I-C

| Cmpd. No | b | $R^{20}$ | $R^{11}$ | $R^{12}$ | $R^{13}$ | $R^{14}$ | $R^{15}$ |
|---|---|---|---|---|---|---|---|
| 75 | 4 | H | H | Cl | H | H | H |
| 76 | 4 | H | Cl | Cl | H | H | H |
| 77 | 4 | H | Cl | H | Cl | H | H |
| 78 | 4 | H | Cl | H | H | Cl | H |
| 79 | 4 | H | Cl | H | H | H | Cl |
| 80 | 4 | H | H | Cl | Cl | H | H |
| 81 | 4 | H | H | Cl | H | Cl | H |
| 82 | 4 | H | H | $C(CH_3)_3$ | H | H | H |
| 83 | 4 | H | H | H | $C(CH_3)_3$ | H | H |
| 84 | 4 | H | $CH_3$ | H | H | H | H |
| 85 | 4 | H | H | $CH_3$ | H | H | H |
| 86 | 4 | H | H | H | $CH_3$ | H | H |
| 87 | 4 | H | H | F | H | F | H |
| 88 | 4 | H | H | H | Cl | $CH_3$ | H |
| 89 | 4 | H | H | H | H | C≡N | H |
| 90 | 4 | H | H | H | I | H | H |
| 91 | 4 | H | H | H | Cl | H | H |
| 92 | 4 | H | H | H | H | H | Cl |
| 93 | 4 | H | H | H | $NO_2$ | H | H |
| 94 | 4 | H | H | H | H | H | H |
| 95 | 4 | H | $OCF_3$ | H | H | H | H |
| 96 | 4 | H | H | $OCF_3$ | H | H | H |
| 97 | 4 | H | H | H | $OCF_3$ | H | H |
| 99 | 4 | H | H | $CH_3$ | $CH_3$ | H | H |
| 100 | 4 | H | H | $CH_3$ | H | $CH_3$ | H |
| 101 | 4 | H | H | H | $CH_3$ | Cl | H |
| 102 | 4 | H | Br | H | H | H | H |

TABLE 1-continued

Phenylalkyl Substituted Cyclic Urea Derivatives

| | | | | | | | |
|---|---|---|---|---|---|---|---|
| 103 | 4 | H | H | Br | H | H | H |
| 104 | 4 | H | H | H | Br | H | H |
| 105 | 2 | H | H | H | $CF_3$ | H | H |
| 106 | 3 | H | H | H | $CF_3$ | H | H |
| 107 | 4 | H | H | H | $CF_3$ | H | H |
| 108 | 4 | H | $CF_3$ | H | H | H | H |
| 109 | 4 | H | H | $CF_3$ | H | H | H |
| 110 | 4 | $CH_3$ | H | H | H | H | H |
| 111 | 4 | $CH_3$ | Cl | H | H | H | H |
| 112 | 4 | $CH_3$ | H | Cl | H | H | H |
| 113 | 4 | $CH_3$ | H | H | Cl | H | H |
| 114 | 4 | $CH_3$ | F | H | H | H | H |
| 115 | 4 | $CH_3$ | H | F | H | H | H |
| 116 | 4 | $CH_3$ | H | H | F | H | H |
| 117 | 4 | $CH_3$ | Cl | Cl | H | H | H |
| 118 | 4 | $CH_3$ | Cl | H | Cl | H | H |
| 119 | 4 | $CH_3$ | Cl | H | H | Cl | H |
| 120 | 4 | $CH_3$ | Cl | H | H | H | Cl |
| 121 | 4 | $CH_3$ | H | Cl | Cl | H | H |
| 122 | 4 | $CH_3$ | H | Cl | H | Cl | H |
| 123 | 4 | $CH_3$ | F | H | Cl | H | H |
| 124 | 4 | $CH_3$ | H | $C(CH_3)_3$ | H | H | H |
| 125 | 4 | $CH_3$ | H | H | $C(CH_3)_3$ | H | H |
| 126 | 4 | $CH_3$ | $CH_3$ | H | H | H | H |
| 127 | 4 | $CH_3$ | H | $CH_3$ | H | H | H |
| 128 | 4 | $CH_3$ | H | H | $CH_3$ | H | H |
| 129 | 4 | $CH_3$ | $CF_3$ | H | H | H | H |
| 130 | 4 | $CH_3$ | H | $CF_3$ | H | H | H |
| 131 | 4 | $CH_3$ | H | H | $CF_3$ | H | H |
| 132 | 4 | $CH_3$ | $OCF_3$ | H | H | H | H |
| 133 | 4 | $CH_3$ | H | $OCF_3$ | H | H | H |
| 134 | 4 | $CH_3$ | H | H | $OCF_3$ | H | H |
| 135 | 4 | $CH_3$ | H | H | $SO_2CHF_2$ | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{14}$ and $R^{15}$ are taken together with —$CR^{24}$=$CR^{25}CR^{26}$=$CR^{27}$— to form a fused ring; providing the following compounds:

I-D

| Cmpd. No | b | $R^{20}$ | $R^{11}$ | $R^{12}$ | $R^{13}$ | $R^{24}$ | $R^{25}$ | $R^{26}$ | $R^{27}$ |
|---|---|---|---|---|---|---|---|---|---|
| 136 | 4 | H | H | H | H | H | H | H | H |
| 137 | 4 | H | Cl | H | H | H | H | H | H |
| 138 | 4 | H | H | Cl | H | H | H | H | H |
| 139 | 4 | H | H | H | Cl | H | H | H | H |
| 140 | 4 | H | H | H | H | Cl | H | H | H |
| 141 | 4 | H | H | H | H | H | Cl | H | H |
| 142 | 4 | H | H | H | H | H | H | Cl | H |
| 143 | 4 | H | H | H | H | H | H | H | Cl |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{12}$ and $R^{13}$ are taken together with —$CR^{24}$=$CR^{25}CR^{26}$=$CR^{27}$— to form a fused ring; providing the following compounds:

I-E

| Cmpd. No | b | $R^{20}$ | $R^{11}$ | $R^{14}$ | $R^{15}$ | $R^{24}$ | $R^{25}$ | $R^{26}$ | $R^{27}$ |
|---|---|---|---|---|---|---|---|---|---|
| 144 | 4 | H | H | H | H | H | H | H | H |
| 145 | 4 | H | Cl | H | H | H | H | H | H |
| 146 | 4 | H | H | Cl | H | H | H | H | H |
| 147 | 4 | H | H | H | Cl | H | H | H | H |
| 148 | 4 | H | H | H | H | Cl | H | H | H |
| 149 | 4 | H | H | H | H | H | Cl | H | H |
| 150 | 4 | H | H | H | H | H | H | Cl | H |
| 151 | 4 | H | H | H | H | H | H | H | Cl |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{11}$ and $R^{12}$ are taken together with —$CH_2CR^{24}CR^{25}O$— to form a benzo-fused ring; providing the following compounds:

I-F

| Cmpd. No | b | $R^{20}$ | $R^{13}$ | $R^{14}$ | $R^{15}$ | $R^{24}$ | $R^{25}$ |
|---|---|---|---|---|---|---|---|
| 152 | 4 | H | H | H | H | $CH_3$ | $CH_3$ |
| 153 | 4 | H | Cl | H | H | $CH_3$ | $CH_3$ |
| 154 | 4 | H | H | Cl | H | $CH_3$ | $CH_3$ |
| 155 | 4 | H | H | H | Cl | $CH_3$ | $CH_3$ |
| 156 | 4 | H | Br | H | H | $CH_3$ | $CH_3$ |
| 157 | 4 | H | H | Br | H | $CH_3$ | $CH_3$ |
| 158 | 4 | H | H | H | Br | $CH_3$ | $CH_3$ |
| 159 | 4 | H | H | H | H | H | H |
| 160 | 4 | H | Cl | H | H | H | H |
| 161 | 4 | H | H | Cl | H | H | H |
| 162 | 4 | H | H | H | Cl | H | H |
| 163 | 4 | H | Br | H | H | H | H |
| 164 | 4 | H | H | Br | H | H | H |
| 165 | 4 | H | H | H | Br | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{11}$ and $R^{12}$ are taken together with —$OCR^{24}CR^{25}O$— to form a benzo-fused ring; providing the following compounds:

TABLE 1-continued

Phenylalkyl Substituted Cyclic Urea Derivatives

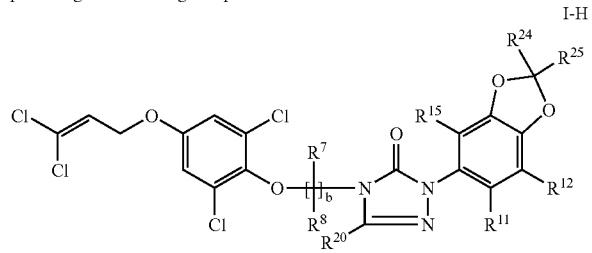

I-G

| Cmpd. No | b | $R^{20}$ | $R^{13}$ | $R^{14}$ | $R^{15}$ | $R^{24}$ | $R^{25}$ |
|---|---|---|---|---|---|---|---|
| 166 | 4 | H | H | H | H | $CH_3$ | $CH_3$ |
| 167 | 4 | H | Cl | H | H | $CH_3$ | $CH_3$ |
| 168 | 4 | H | H | Cl | H | $CH_3$ | $CH_3$ |
| 169 | 4 | H | H | H | Cl | $CH_3$ | $CH_3$ |
| 170 | 4 | H | Br | H | H | $CH_3$ | $CH_3$ |
| 171 | 4 | H | H | Br | H | $CH_3$ | $CH_3$ |
| 172 | 4 | H | H | H | Br | $CH_3$ | $CH_3$ |
| 173 | 4 | H | H | H | H | F | F |
| 174 | 4 | H | Cl | H | H | F | F |
| 175 | 4 | H | H | Cl | H | F | F |
| 176 | 4 | H | H | H | Cl | F | F |
| 177 | 4 | H | Br | H | H | F | F |
| 178 | 4 | H | H | Br | H | F | F |
| 179 | 4 | H | H | H | Br | F | F |
| 180 | 4 | H | H | H | H | H | H |
| 181 | 4 | H | Cl | H | H | H | H |
| 182 | 4 | H | H | Cl | H | H | H |
| 183 | 4 | H | H | H | Cl | H | H |
| 184 | 4 | H | Br | H | H | H | H |
| 185 | 4 | H | H | Br | H | H | H |
| 186 | 4 | H | H | H | Br | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{13}$ and $R^{14}$ are taken together with —$OCR^{24}R^{25}O$— to form a benzo-fused ring; providing the following compounds:

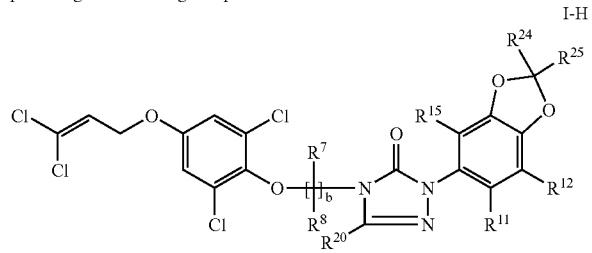

I-H

| Cmpd. No | b | $R^{20}$ | $R^{11}$ | $R^{12}$ | $R^{15}$ | $R^{24}$ | $R^{25}$ |
|---|---|---|---|---|---|---|---|
| 187 | 4 | H | H | H | H | $CH_3$ | $CH_3$ |
| 188 | 4 | H | Cl | H | H | $CH_3$ | $CH_3$ |
| 189 | 4 | H | H | Cl | H | $CH_3$ | $CH_3$ |
| 190 | 4 | H | H | H | Cl | $CH_3$ | $CH_3$ |
| 191 | 4 | H | Br | H | H | $CH_3$ | $CH_3$ |
| 192 | 4 | H | H | Br | H | $CH_3$ | $CH_3$ |
| 193 | 4 | H | H | H | Br | $CH_3$ | $CH_3$ |
| 194 | 4 | H | H | H | H | F | F |
| 195 | 4 | H | Cl | H | H | F | F |
| 196 | 4 | H | H | Cl | H | F | F |
| 197 | 4 | H | H | H | Cl | F | F |
| 198 | 4 | H | Br | H | H | F | F |
| 199 | 4 | H | H | Br | H | F | F |
| 200 | 4 | H | H | H | Br | F | F |
| 201 | 4 | H | H | H | H | H | H |
| 202 | 4 | H | Cl | H | H | H | H |
| 203 | 4 | H | H | Cl | H | H | H |
| 204 | 4 | H | H | H | Cl | H | H |
| 205 | 4 | H | Br | H | H | H | H |
| 206 | 4 | H | H | Br | H | H | H |
| 207 | 4 | H | H | H | Br | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{11}$ and $R^{12}$ are taken together with —$OCR^{24}R^{25}CR^{26}R^{27}O$— to form a benzo-fused ring; providing the following compounds:

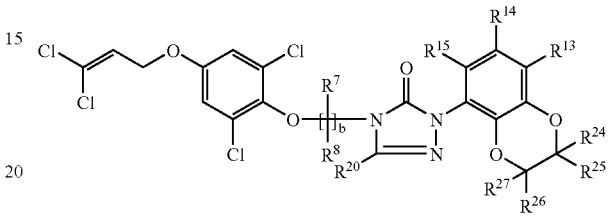

I-J

| Cmpd. No | b | $R^{20}$ | $R^{13}$ | $R^{14}$ | $R^{15}$ | $R^{24}$ | $R^{25}$ | $R^{26}$ | $R^{27}$ |
|---|---|---|---|---|---|---|---|---|---|
| 208 | 4 | H | H | H | H | H | H | H | H |
| 209 | 4 | H | Cl | H | H | H | H | H | H |
| 210 | 4 | H | H | Cl | H | H | H | H | H |
| 211 | 4 | H | H | H | Cl | H | H | H | H |
| 212 | 4 | H | Br | H | H | H | H | H | H |
| 213 | 4 | H | H | Br | H | H | H | H | H |
| 214 | 4 | H | H | H | Br | H | H | H | H |
| 215 | 4 | H | H | H | H | F | F | F | F |
| 216 | 4 | H | Cl | H | H | F | F | F | F |
| 217 | 4 | H | H | Cl | H | F | F | F | F |
| 218 | 4 | H | H | H | Cl | F | F | F | F |
| 219 | 4 | H | Br | H | H | F | F | F | F |
| 220 | 4 | H | H | Br | H | F | F | F | F |
| 221 | 4 | H | H | H | Br | F | F | F | F |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —$CR^{20}$=N—; c and d are 0; X is aryl substituted with $R^{11}$ through $R^{15}$, and $R^{13}$ and $R^{14}$ are taken together with —$OCR^{24}R^{25}CR^{26}R^{27}O$— to form a benzo-fused ring; providing the following compounds:

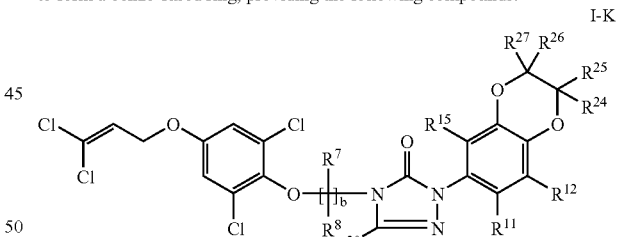

I-K

| Cmpd. No | b | $R^{20}$ | $R^{11}$ | $R^{12}$ | $R^{15}$ | $R^{24}$ | $R^{25}$ | $R^{26}$ | $R^{27}$ |
|---|---|---|---|---|---|---|---|---|---|
| 222 | 4 | H | H | H | H | H | H | H | H |
| 223 | 4 | H | Cl | H | H | H | H | H | H |
| 224 | 4 | H | H | Cl | H | H | H | H | H |
| 225 | 4 | H | H | H | Cl | H | H | H | H |
| 226 | 4 | H | Br | H | H | H | H | H | H |
| 227 | 4 | H | H | Br | H | H | H | H | H |
| 228 | 4 | H | H | H | Br | H | H | H | H |
| 229 | 4 | H | H | H | H | F | F | F | F |
| 230 | 4 | H | Cl | H | H | F | F | F | F |
| 231 | 4 | H | H | Cl | H | F | F | F | F |
| 232 | 4 | H | H | H | Cl | F | F | F | F |
| 233 | 4 | H | Br | H | H | F | F | F | F |
| 234 | 4 | H | H | Br | H | F | F | F | F |
| 235 | 4 | H | H | H | Br | F | F | F | F |

TABLE 1-continued

Phenylalkyl Substituted Cyclic Urea Derivatives

Where $R^1$, $R^2$, $R^4$ $R^7$, $R^8$ are hydrogen;
R, $R^3$, $R^5$ and $R^6$ are chlorine; A is $(CH_2)_f$
where f is 1; B and G are O, a is 1, and D is O; E is —$CR^{20}$=N—;
c and d are 0; X is aryl substituted with $R^{11}$ through $R^{15}$,
and $R^{11}$ and $R^{12}$ are taken together with —$NCR^{24}S$—
to form a benzo-fused ring; providing the following compounds:

I-L

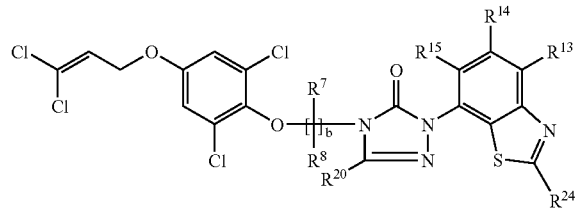

| Cmpd. No | b | $R^{20}$ | $R^{13}$ | $R^{14}$ | $R^{15}$ | $R^{24}$ |
|---|---|---|---|---|---|---|
| 236 | 4 | H | H | H | H | H |
| 237 | 4 | H | Cl | H | H | H |
| 238 | 4 | H | H | Cl | H | H |
| 239 | 4 | H | H | H | Cl | H |
| 240 | 4 | H | Br | H | H | H |
| 241 | 4 | H | H | Br | H | H |
| 242 | 4 | H | H | H | Br | H |
| 243 | 4 | H | H | H | H | $CH_3$ |
| 244 | 4 | H | Cl | H | H | $CH_3$ |
| 245 | 4 | H | H | Cl | H | $CH_3$ |
| 246 | 4 | H | H | H | Cl | $CH_3$ |
| 247 | 4 | H | Br | H | H | $CH_3$ |
| 248 | 4 | H | H | Br | H | $CH_3$ |
| 249 | 4 | H | H | H | Br | $CH_3$ |
| 250 | 4 | H | H | H | H | $CF_3$ |
| 251 | 4 | H | Cl | H | H | $CF_3$ |
| 252 | 4 | H | H | Cl | H | $CF_3$ |
| 253 | 4 | H | H | H | Cl | $CF_3$ |
| 254 | 4 | H | Br | H | H | $CF_3$ |
| 255 | 4 | H | H | Br | H | $CF_3$ |
| 256 | 4 | H | H | H | Br | $CF_3$ |

Where $R^1$, $R^2$, $R^4$ $R^7$, $R^8$ are hydrogen;
R, $R^3$, $R^5$ and $R^6$ are chlorine; A is $(CH_2)_f$
where f is 1; B and G are O, a is 1, and D is O; E is —$CR^{20}$=N—;
c and d are 0; X is heteroaryl substituted with $R^{12}$ through $R^{15}$;
providing the following compounds:

I-M

| Cmpd. No | b | $R^{20}$ | $R^{12}$ | $R^{13}$ | $R^{14}$ | $R^{15}$ |
|---|---|---|---|---|---|---|
| 257 | 4 | H | H | H | H | H |
| 258 | 4 | H | Cl | H | H | H |
| 259 | 4 | H | H | Cl | H | H |
| 260 | 4 | H | H | H | Cl | H |
| 261 | 4 | H | H | H | H | Cl |
| 262 | 4 | H | $CF_3$ | H | H | H |
| 263 | 4 | H | H | $CF_3$ | H | H |
| 264 | 4 | H | H | H | $CF_3$ | H |
| 265 | 4 | H | H | H | H | $CF_3$ |
| 266 | 4 | H | $CH_3$ | H | H | H |
| 267 | 4 | H | H | $CH_3$ | H | H |
| 268 | 4 | H | H | H | $CH_3$ | H |
| 269 | 4 | H | H | H | H | $CH_3$ |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —$CR^{20}$=N—; c and d are 0; X is
heteroaryl substituted with $R^{11}$ through $R^{13}$ and $R^{15}$;
providing the following compounds:

I-N

| Cmpd. No | b | $R^{20}$ | $R^{11}$ | $R^{12}$ | $R^{13}$ | $R^{15}$ |
|---|---|---|---|---|---|---|
| 270 | 4 | H | H | H | H | H |
| 271 | 4 | H | Cl | H | H | H |
| 272 | 4 | H | H | Cl | H | H |
| 273 | 4 | H | H | H | Cl | H |
| 274 | 4 | H | H | H | H | Cl |
| 275 | 4 | H | $CF_3$ | H | H | H |
| 276 | 4 | H | H | $CF_3$ | H | H |
| 277 | 4 | H | H | H | $CF_3$ | H |
| 278 | 4 | H | H | H | H | $CF_3$ |
| 279 | 4 | H | $CH_3$ | H | H | H |
| 280 | 4 | H | H | $CH_3$ | H | H |
| 281 | 4 | H | H | H | $CH_3$ | H |
| 282 | 4 | H | H | H | H | $CH_3$ |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —$CR^{20}$=N—; c and d are 0; X is
heteroaryl substituted with $R^{11}$, $R^{12}$, $R^{14}$ and $R^{15}$;
providing the following compounds:

I-O

| Cmpd. No | b | $R^{20}$ | $R^{11}$ | $R^{12}$ | $R^{14}$ | $R^{15}$ |
|---|---|---|---|---|---|---|
| 283 | 4 | H | H | H | H | H |
| 284 | 4 | H | Cl | H | H | H |
| 285 | 4 | H | H | Cl | H | H |
| 286 | 4 | H | $CF_3$ | H | H | H |
| 287 | 4 | H | H | $CF_3$ | H | H |
| 288 | 4 | H | $CH_3$ | H | H | H |
| 289 | 4 | H | H | $CH_3$ | H | H |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —N=N—; c and d are 0; X is
aryl substituted with $R^{11}$ through $R^{15}$;
providing the following compounds:

I-P

| Cmpd. No | b | $R^{11}$ | $R^{12}$ | $R^{13}$ | $R^{14}$ | $R^{15}$ |
|---|---|---|---|---|---|---|
| 290 | 4 | H | H | H | H | H |
| 291 | 4 | H | H | $C(CH_3)_3$ | H | H |

TABLE 1-continued

Phenylalkyl Substituted Cyclic Urea Derivatives

| | b | R¹¹/R... | | | | |
|---|---|---|---|---|---|---|
| 292 | 4 | H | C(CH₃)₃ | H | H | H |
| 293 | 4 | H | H | CF₃ | H | H |
| 294 | 4 | Cl | H | H | H | H |
| 295 | 4 | Cl | Cl | H | H | H |
| 296 | 4 | Cl | H | Cl | H | H |
| 297 | 4 | Cl | H | H | Cl | H |
| 298 | 4 | Cl | H | H | H | Cl |
| 299 | 4 | H | Cl | H | Cl | H |
| 300 | 4 | H | H | Cl | H | H |
| 301 | 4 | OCF₃ | H | H | H | H |
| 302 | 4 | H | OCF₃ | H | H | H |
| 303 | 4 | H | H | OCF₃ | H | H |
| 304 | 4 | H | CF₃ | H | H | H |
| 305 | 4 | CF₃ | H | H | H | H |
| 306 | 4 | H | Cl | Cl | H | H |
| 307 | 4 | H | H | H | H | H |
| 308 | 2 | H | Cl | H | H | H |
| 309 | 3 | H | Cl | H | H | H |
| 310 | 4 | H | Cl | H | H | H |
| 311 | 5 | H | Cl | H | H | H |
| 312 | 4 | CH₃ | H | H | H | H |
| 313 | 4 | H | CH₃ | H | H | H |
| 314 | 4 | H | H | CH₃ | H | H |
| 315 | 4 | Br | H | H | H | H |
| 316 | 4 | H | Br | H | H | H |
| 317 | 4 | H | H | Br | H | H |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —N=N—; c and d are 0; X is aryl substituted with $R^{11}$ through $R^{15}$, and $R^{14}$ and $R^{15}$ are taken together with —$CR^{24}$=$CR^{25}CR^{26}$=$CR^{27}$— to form a fused ring; providing the following compounds:

I-Q

Cmpd.
| No | b | R¹¹ | R¹² | R¹³ | R²⁴ | R²⁵ | R²⁶ | R²⁷ |
|---|---|---|---|---|---|---|---|---|
| 318 | 4 | H | H | H | H | H | H | H |
| 319 | 4 | Cl | H | H | H | H | H | H |
| 320 | 4 | H | Cl | H | H | H | H | H |
| 321 | 4 | H | H | Cl | H | H | H | H |
| 322 | 4 | H | H | H | Cl | H | H | H |
| 323 | 4 | H | H | H | H | Cl | H | H |
| 324 | 4 | H | H | H | H | H | Cl | H |
| 325 | 4 | H | H | H | H | H | H | Cl |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —N=N—; c and d are 0; X is aryl substituted with $R^{11}$ through $R^{15}$, and $R^{12}$ and $R^{13}$ are taken together with —$CR^{24}$=$CR^{25}CR^{26}$=$CR^{27}$— to form a fused ring; providing the following compounds:

I-R

Cmpd.
| No | b | R¹¹ | R¹⁴ | R¹⁵ | R²⁴ | R²⁵ | R²⁶ | R²⁷ |
|---|---|---|---|---|---|---|---|---|
| 326 | 4 | H | H | H | H | H | H | H |
| 327 | 4 | Cl | H | H | H | H | H | H |
| 328 | 4 | H | Cl | H | H | H | H | H |
| 329 | 4 | H | H | Cl | H | H | H | H |
| 330 | 4 | H | H | H | Cl | H | H | H |
| 331 | 4 | H | H | H | H | Cl | H | H |
| 332 | 4 | H | H | H | H | H | Cl | H |
| 333 | 4 | H | H | H | H | H | H | Cl |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —N=N—; c and d are 0; X is aryl substituted with $R^{11}$ through $R^{15}$, and $R^{11}$ and $R^{12}$ are taken together with —$CH_2CR^{24}R^{25}O$— to form a benzo-fused ring; providing the following compounds:

I-S

Cmpd.
| No | b | R¹³ | R¹⁴ | R¹⁵ | R²⁴ | R²⁵ |
|---|---|---|---|---|---|---|
| 334 | 5 | H | H | H | CH₃ | CH₃ |
| 335 | 4 | H | H | H | CH₃ | CH₃ |
| 336 | 3 | H | H | H | CH₃ | CH₃ |
| 337 | 2 | H | H | H | CH₃ | CH₃ |
| 338 | 4 | H | H | H | H | H |
| 339 | 4 | Cl | H | H | CH₃ | CH₃ |
| 340 | 4 | H | Cl | H | CH₃ | CH₃ |
| 341 | 4 | H | H | Cl | CH₃ | CH₃ |
| 342 | 4 | F | H | H | CH₃ | CH₃ |
| 343 | 4 | H | F | H | CH₃ | CH₃ |
| 344 | 4 | H | H | F | CH₃ | CH₃ |
| 345 | 4 | Br | H | H | CH₃ | CH₃ |
| 346 | 4 | H | Br | H | CH₃ | CH₃ |
| 347 | 4 | H | H | Br | CH₃ | CH₃ |
| 348 | 4 | CH₃ | H | H | CH₃ | CH₃ |
| 349 | 4 | H | CH₃ | H | CH₃ | CH₃ |
| 350 | 4 | H | H | CH₃ | CH₃ | CH₃ |

Where $R^1$, $R^2$, $R^4$ $R^7$, $R^8$ are hydrogen; R, $R^3$, $R^5$ and $R^6$ are chlorine; A is $(CH_2)_f$ where f is 1; B and G are O, a is 1, and D is O; E is —N=N—; c and d are 0; X is aryl substituted with $R^{11}$ through $R^{15}$, and $R^{11}$ and $R^{12}$ are taken together with —$OCR^{24}R^{25}O$— to form a benzo-fused ring; providing the following compounds:

TABLE 1-continued

Phenylalkyl Substituted Cyclic Urea Derivatives

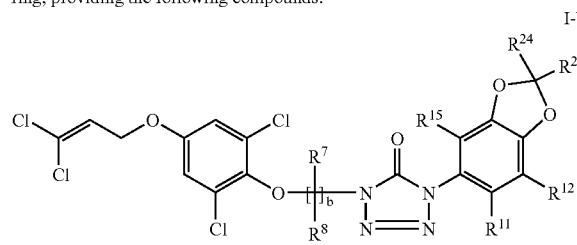

I-T

| Cmpd. No | b | $R^{13}$ | $R^{14}$ | $R^{15}$ | $R^{24}$ | $R^{25}$ |
|---|---|---|---|---|---|---|
| 351 | 4 | H | H | H | CH₃ | CH₃ |
| 352 | 4 | Cl | H | H | CH₃ | CH₃ |
| 353 | 4 | H | Cl | H | CH₃ | CH₃ |
| 354 | 4 | H | H | Cl | CH₃ | CH₃ |
| 355 | 4 | Br | H | H | CH₃ | CH₃ |
| 356 | 4 | H | Br | H | CH₃ | CH₃ |
| 357 | 4 | H | H | Br | CH₃ | CH₃ |
| 358 | 4 | H | H | H | H | H |
| 359 | 4 | Cl | H | H | H | H |
| 360 | 4 | H | Cl | H | H | H |
| 361 | 4 | H | H | Cl | H | H |
| 362 | 4 | Br | H | H | H | H |
| 363 | 4 | H | Br | H | H | H |
| 364 | 4 | H | H | Br | H | H |
| 365 | 4 | H | H | H | F | F |
| 366 | 4 | Cl | H | H | F | F |
| 367 | 4 | H | Cl | H | F | F |
| 368 | 4 | H | H | Cl | F | F |
| 369 | 4 | Br | H | H | F | F |
| 370 | 4 | H | Br | H | F | F |
| 371 | 4 | H | H | Br | F | F |

Where $R^1$, $R^2$, $R^4$ $R^7$, $R^8$ are hydrogen; R, $R^3$, $R^5$ and $R^6$ are chlorine; A is (CH₂)$_f$ where f is 1; B and G are O, a is 1, and D is O; E is —N═N—; c and d are 0; X is aryl substituted with $R^{11}$ through $R^{15}$, and $R^{13}$ and $R^{14}$ are taken together with —OCR$^{24}$R$^{25}$O— to form a benzo-fused ring; providing the following compounds:

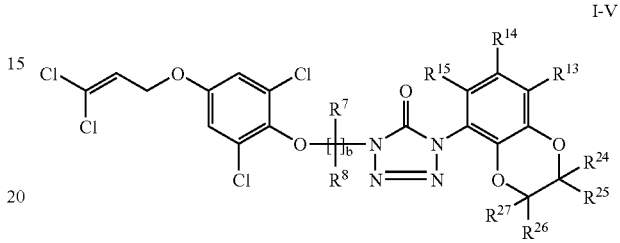

I-U

| Cmpd. No | b | $R^{11}$ | $R^{12}$ | $R^{15}$ | $R^{24}$ | $R^{25}$ |
|---|---|---|---|---|---|---|
| 372 | 4 | H | H | H | CH₃ | CH₃ |
| 373 | 4 | Cl | H | H | CH₃ | CH₃ |
| 374 | 4 | H | Cl | H | CH₃ | CH₃ |
| 375 | 4 | H | H | Cl | CH₃ | CH₃ |
| 376 | 4 | Br | H | H | CH₃ | CH₃ |
| 377 | 4 | H | Br | H | CH₃ | CH₃ |
| 378 | 4 | H | H | Br | CH₃ | CH₃ |
| 379 | 4 | H | H | H | H | H |
| 380 | 4 | Cl | H | H | H | H |
| 381 | 4 | H | Cl | H | H | H |
| 382 | 4 | H | H | Cl | H | H |
| 383 | 4 | Br | H | H | H | H |
| 384 | 4 | H | Br | H | H | H |
| 385 | 4 | H | H | Br | H | H |
| 386 | 4 | H | H | H | F | F |
| 387 | 4 | Cl | H | H | F | F |
| 388 | 4 | H | Cl | H | F | F |
| 389 | 4 | H | H | Cl | F | F |
| 390 | 4 | Br | H | H | F | F |
| 391 | 4 | H | Br | H | F | F |
| 392 | 4 | H | H | Br | F | F |

Where $R^1$, $R^2$, $R^4$ $R^7$, $R^8$ are hydrogen; R, $R^3$, $R^5$ and $R^6$ are chlorine; A is (CH₂)$_f$ where f is 1; B and G are O, a is 1, and D is O; E is —N═N—; c and d are 0; X is aryl substituted with $R^{11}$ through $R^{15}$, and $R^{11}$ and $R^{12}$ are taken together with —OCR$^{24}$R$^{25}$CR$^{26}$R$^{27}$O— to form a benzo-fused ring; providing the following compounds:

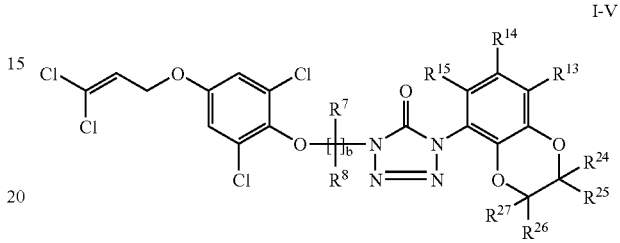

I-V

| Cmpd. No | b | $R^{13}$ | $R^{14}$ | $R^{15}$ | $R^{24}$ | $R^{25}$ | $R^{26}$ | $R^{27}$ |
|---|---|---|---|---|---|---|---|---|
| 393 | 4 | H | H | H | H | H | H | H |
| 394 | 4 | Cl | H | H | H | H | H | H |
| 395 | 4 | H | Cl | H | H | H | H | H |
| 396 | 4 | H | H | Cl | H | H | H | H |
| 397 | 4 | Br | H | H | H | H | H | H |
| 398 | 4 | H | Br | H | H | H | H | H |
| 399 | 4 | H | H | Br | H | H | H | H |
| 400 | 4 | H | H | H | F | F | F | F |
| 401 | 4 | Cl | H | H | F | F | F | F |
| 402 | 4 | H | Cl | H | F | F | F | F |
| 403 | 4 | H | H | Cl | F | F | F | F |
| 404 | 4 | Br | H | H | F | F | F | F |
| 405 | 4 | H | Br | H | F | F | F | F |
| 406 | 4 | H | H | Br | F | F | F | F |

Where $R^1$, $R^2$, $R^4$ $R^7$, $R^8$ are hydrogen; R, $R^3$, $R^5$ and $R^6$ are chlorine; A is (CH₂)$_f$ where f is 1; B and G are O, a is 1, and D is O; E is —N═N—; c and d are 0; X is aryl substituted with $R^{11}$ through $R^{15}$, and $R^{13}$ and $R^{14}$ are taken together with —OCR$^{24}$R$^{25}$CR$^{26}$R$^{27}$O— to form a benzo-fused ring; providing the following compounds:

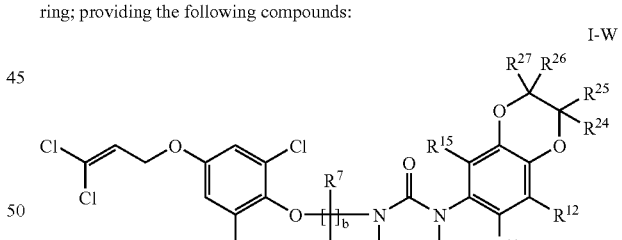

I-W

| Cmpd. No | b | $R^{11}$ | $R^{12}$ | $R^{15}$ | $R^{24}$ | $R^{25}$ | $R^{26}$ | $R^{27}$ |
|---|---|---|---|---|---|---|---|---|
| 407 | 4 | H | H | H | H | H | H | H |
| 408 | 4 | Cl | H | H | H | H | H | H |
| 409 | 4 | H | Cl | H | H | H | H | H |
| 410 | 4 | H | H | Cl | H | H | H | H |
| 411 | 4 | Br | H | H | H | H | H | H |
| 412 | 4 | H | Br | H | H | H | H | H |
| 413 | 4 | H | H | Br | H | H | H | H |
| 414 | 4 | H | H | H | F | F | F | F |
| 415 | 4 | Cl | H | H | F | F | F | F |
| 416 | 4 | H | Cl | H | F | F | F | F |
| 417 | 4 | H | H | Cl | F | F | F | F |
| 418 | 4 | Br | H | H | F | F | F | F |

TABLE 1-continued

Phenylalkyl Substituted Cyclic Urea Derivatives

| 419 | 4 | H | Br | H | F | F | F | F |
| 420 | 4 | H | H | Br | F | F | F | F |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —N=N—; c and d are 0; X is
aryl substituted with $R^{11}$ through $R^{15}$, and $R^{11}$ and $R^{12}$ are taken
together with —$NCR^{24}S$— to form a benzo-fused
ring; providing the following compounds:

I-X

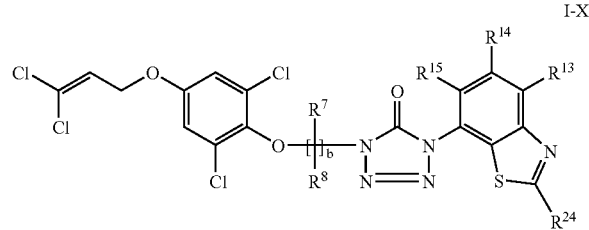

| Cmpd. No | b | $R^{13}$ | $R^{14}$ | $R^{15}$ | $R^{24}$ |
|---|---|---|---|---|---|
| 421 | 4 | H | H | H | H |
| 422 | 4 | Cl | H | H | H |
| 423 | 4 | H | Cl | H | H |
| 424 | 4 | H | H | Cl | H |
| 425 | 4 | Br | H | H | H |
| 426 | 4 | H | Br | H | H |
| 427 | 4 | H | H | Br | H |
| 428 | 4 | H | H | H | $CH_3$ |
| 429 | 4 | Cl | H | H | $CH_3$ |
| 430 | 4 | H | Cl | H | $CH_3$ |
| 431 | 4 | H | H | Cl | $CH_3$ |
| 432 | 4 | Br | H | H | $CH_3$ |
| 433 | 4 | H | Br | H | $CH_3$ |
| 434 | 4 | H | H | Br | $CH_3$ |
| 435 | 4 | H | H | H | $CF_3$ |
| 436 | 4 | Cl | H | H | $CF_3$ |
| 437 | 4 | H | Cl | H | $CF_3$ |
| 438 | 4 | H | H | Cl | $CF_3$ |
| 439 | 4 | Br | H | H | $CF_3$ |
| 440 | 4 | H | Br | H | $CF_3$ |
| 441 | 4 | H | H | Br | $CF_3$ |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —N=N—; c and d are 0; X is
heteroaryl substituted with $R^{12}$ through $R^{15}$;
providing the following compounds:

I-Y

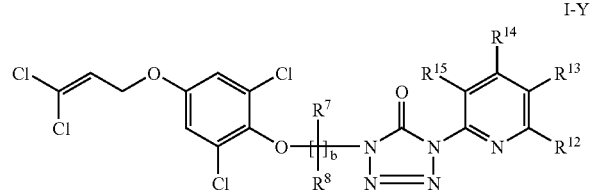

| Cmpd. No | b | $R^{12}$ | $R^{13}$ | $R^{14}$ | $R^{15}$ |
|---|---|---|---|---|---|
| 442 | 4 | H | H | H | H |
| 443 | 4 | Cl | H | H | H |
| 444 | 4 | H | Cl | H | H |
| 445 | 4 | H | H | Cl | H |
| 446 | 4 | H | H | H | Cl |
| 447 | 4 | $CF_3$ | H | H | H |
| 448 | 4 | H | $CF_3$ | H | H |
| 449 | 4 | H | H | $CF_3$ | H |
| 450 | 4 | H | H | H | $CF_3$ |
| 451 | 4 | $CH_3$ | H | H | H |
| 452 | 4 | H | $CH_3$ | H | H |
| 453 | 4 | H | H | $CH_3$ | H |
| 454 | 4 | H | H | H | $CH_3$ |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —N=N—; c and d are 0; X is
heteroaryl substituted with $R^{11}$ through $R^{13}$ and $R^{15}$;
providing the following compounds:

I-Z

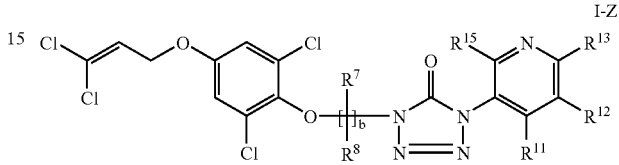

| Cmpd. No | b | $R^{11}$ | $R^{12}$ | $R^{13}$ | $R^{15}$ |
|---|---|---|---|---|---|
| 455 | 4 | H | H | H | H |
| 456 | 4 | Cl | H | H | H |
| 457 | 4 | H | Cl | H | H |
| 458 | 4 | H | H | Cl | H |
| 459 | 4 | H | H | H | Cl |
| 460 | 4 | $CF_3$ | H | H | H |
| 461 | 4 | H | $CF_3$ | H | H |
| 462 | 4 | H | H | $CF_3$ | H |
| 463 | 4 | H | H | H | $CF_3$ |
| 464 | 4 | $CH_3$ | H | H | H |
| 465 | 4 | H | $CH_3$ | H | H |
| 466 | 4 | H | H | $CH_3$ | H |
| 467 | 4 | H | H | H | $CH_3$ |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —N=N—; c and d are 0; X is
heteroaryl substituted with $R^{11}$, $R^{12}$, $R^{14}$ and $R^{15}$;
providing the following compounds:

I-AA

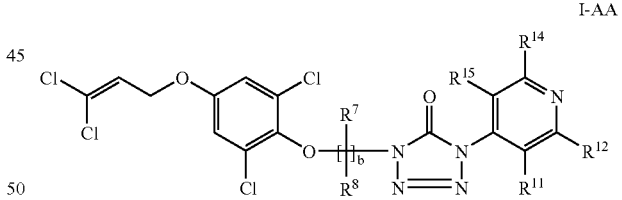

| Cmpd. No | b | $R^{11}$ | $R^{12}$ | $R^{14}$ | $R^{15}$ |
|---|---|---|---|---|---|
| 468 | 4 | H | H | H | H |
| 469 | 4 | Cl | H | H | H |
| 470 | 4 | H | Cl | H | H |
| 471 | 4 | $CF_3$ | H | H | H |
| 472 | 4 | H | $CF_3$ | H | H |
| 473 | 4 | $CH_3$ | H | H | H |
| 474 | 4 | H | $CH_3$ | H | H |

Where $R^1$, $R^2$, $R^4$ $R^7$, $R^8$, $R^9$, $R^{10}$ are hydrogen; R, $R^3$,
$R^5$ and $R^6$ are chlorine; A is $(CH_2)_f$ where f is 1; B and G are O,
a is 1, and D is O; E is —$CR^{20}$=N—; c is 1 and d is 0; X is
aryl substituted with $R^{11}$ through $R^{15}$; providing the following compounds:

TABLE 1-continued

Phenylalkyl Substituted Cyclic Urea Derivatives

I-BB

| Cmpd. No | b | $R^{20}$ | $R^{11}$ | $R^{12}$ | $R^{13}$ | $R^{14}$ | $R^{15}$ |
|---|---|---|---|---|---|---|---|
| 475 | 4 | H | H | H | H | H | H |
| 476 | 4 | H | Cl | H | H | H | H |
| 477 | 4 | H | H | Cl | H | H | H |
| 478 | 4 | H | H | H | Cl | H | H |
| 479 | 4 | H | Cl | Cl | H | H | H |
| 480 | 4 | H | Cl | H | Cl | H | H |
| 481 | 4 | H | Cl | H | H | Cl | H |
| 482 | 4 | H | Cl | H | H | H | Cl |
| 483 | 4 | H | H | Cl | Cl | H | H |
| 484 | 4 | H | H | Cl | H | Cl | H |
| 485 | 4 | H | $CF_3$ | H | H | H | H |
| 486 | 4 | H | H | $CF_3$ | H | H | H |
| 487 | 4 | H | H | H | $CF_3$ | H | H |
| 488 | 4 | H | $OCF_3$ | H | H | H | H |
| 489 | 4 | H | H | $OCF_3$ | H | H | H |
| 490 | 4 | H | H | H | $OCF_3$ | H | H |
| 491 | 4 | H | $CH_3$ | H | H | H | H |
| 492 | 4 | H | H | $CH_3$ | H | H | H |
| 493 | 4 | H | H | H | $CH_3$ | H | H |
| 494 | 4 | H | $CH_3$ | $CH_3$ | H | H | H |
| 495 | 4 | H | $CH_3$ | H | $CH_3$ | H | H |
| 496 | 4 | H | $CH_3$ | H | H | $CH_3$ | H |
| 497 | 4 | H | $CH_3$ | H | H | H | $CH_3$ |
| 498 | 4 | H | H | $CH_3$ | $CH_3$ | H | H |
| 499 | 4 | H | H | $CH_3$ | H | $CH_3$ | H |
| 500 | 4 | H | F | H | H | H | H |
| 501 | 4 | H | H | F | H | H | H |
| 502 | 4 | H | H | H | F | H | H |
| 503 | 4 | H | F | F | H | H | H |
| 504 | 4 | H | F | H | F | H | H |
| 505 | 4 | H | F | H | H | F | H |
| 506 | 4 | H | F | H | H | H | F |
| 507 | 4 | H | H | F | F | H | H |
| 508 | 4 | H | H | F | H | F | H |
| 509 | 4 | H | Br | H | H | H | H |
| 510 | 4 | H | H | Br | H | H | H |
| 511 | 4 | H | H | H | Br | H | H |

Where $R^1$, $R^2$, $R^4$ $R^7$, $R^8$, $R^9$, $R^{10}$ are hydrogen; R, $R^3$, $R^5$ and $R^6$ are chlorine; A is $(CH_2)_f$ where f is 1; B and G are O, a is 1, and D is O; E is —N=N—; c is 1 and d is 0; X is aryl substituted with $R^{11}$ through $R^{15}$; providing the following compounds:

I-CC

| Cmpd. No | B | $R^{11}$ | $R^{12}$ | $R^{13}$ | $R^{14}$ | $R^{15}$ |
|---|---|---|---|---|---|---|
| 512 | 4 | H | H | H | H | H |
| 513 | 4 | Cl | H | H | H | H |
| 514 | 4 | H | Cl | H | H | H |
| 515 | 4 | H | H | Cl | H | H |
| 516 | 4 | Cl | Cl | H | H | H |
| 517 | 4 | Cl | H | Cl | H | H |
| 518 | 4 | Cl | H | H | Cl | H |
| 519 | 4 | Cl | H | H | H | Cl |
| 520 | 4 | H | Cl | Cl | H | H |
| 521 | 4 | H | Cl | H | Cl | H |
| 522 | 2 | Cl | H | H | H | H |
| 523 | 3 | Cl | H | H | H | H |
| 524 | 4 | $CH_3$ | H | H | H | H |
| 525 | 4 | H | $CH_3$ | H | H | H |
| 526 | 4 | H | H | $CH_3$ | H | H |
| 527 | 4 | $CF_3$ | H | H | H | H |
| 528 | 4 | H | $CF_3$ | H | H | H |
| 529 | 4 | H | H | $CF_3$ | H | H |
| 530 | 4 | $OCF_3$ | H | H | H | H |
| 531 | 4 | H | $OCF_3$ | H | H | H |
| 532 | 4 | H | H | $OCF_3$ | H | H |

Where $R^1$, $R^2$, $R^4$ $R^7$, $R^8$, $R^9$, $R^{10}$ are hydrogen; R, $R^3$, $R^5$ and $R^6$ are chlorine; A is $(CH_2)_f$ where f is 1; B and G are O, a is 1, and D is O; E is —N=$CR^{20}$—; c is 1 and d is 0; X is aryl substituted with $R^{11}$ through $R^{15}$; providing the following compounds:

I-DD

| Cmpd. No | B | $R^{20}$ | $R^{11}$ | $R^{12}$ | $R^{13}$ | $R^{14}$ | $R^{15}$ |
|---|---|---|---|---|---|---|---|
| 533 | 4 | H | H | H | H | H | H |
| 534 | 4 | H | Cl | H | H | H | H |
| 535 | 4 | H | H | Cl | H | H | H |
| 536 | 3 | H | H | H | Cl | H | H |
| 537 | 4 | H | H | H | Cl | H | H |
| 538 | 4 | H | Cl | Cl | H | H | H |
| 539 | 4 | H | Cl | H | Cl | H | H |
| 540 | 4 | H | Cl | H | H | Cl | H |
| 541 | 4 | H | Cl | H | H | H | Cl |
| 542 | 4 | H | H | Cl | Cl | H | H |
| 543 | 4 | H | H | Cl | H | Cl | H |
| 544 | 4 | H | $CF_3$ | H | H | H | H |
| 545 | 4 | H | H | $CF_3$ | H | H | H |
| 546 | 4 | H | H | H | $CF_3$ | H | H |
| 547 | 3 | H | H | H | $CF_3$ | H | H |
| 548 | 2 | H | H | H | $CF_3$ | H | H |
| 549 | 4 | H | $OCF_3$ | H | H | H | H |
| 550 | 4 | H | H | $OCF_3$ | H | H | H |
| 551 | 4 | H | H | H | $OCF_3$ | H | H |
| 552 | 4 | H | $CH_3$ | H | H | H | H |
| 553 | 4 | H | H | $CH_3$ | H | H | H |
| 554 | 4 | H | H | H | $CH_3$ | H | H |
| 555 | 4 | H | $CH_3$ | $CH_3$ | H | H | H |
| 556 | 4 | H | $CH_3$ | H | $CH_3$ | H | H |
| 557 | 4 | H | $CH_3$ | H | H | $CH_3$ | H |
| 558 | 4 | H | $CH_3$ | H | H | H | $CH_3$ |
| 559 | 4 | H | H | $CH_3$ | $CH_3$ | H | H |
| 560 | 4 | H | H | $CH_3$ | H | $CH_3$ | H |
| 561 | 4 | H | F | H | H | H | H |
| 562 | 4 | H | H | F | H | H | H |
| 563 | 4 | H | H | H | F | H | H |
| 564 | 4 | H | F | F | H | H | H |
| 565 | 4 | H | F | H | F | H | H |
| 566 | 4 | H | F | H | H | F | H |
| 567 | 4 | H | F | H | H | H | F |
| 568 | 4 | H | H | F | F | H | H |
| 569 | 4 | H | H | F | H | F | H |
| 570 | 4 | H | Br | H | H | H | H |
| 571 | 4 | H | H | Br | H | H | H |
| 572 | 4 | H | H | H | Br | H | H |

Where $R^1$, $R^2$, $R^4$ $R^7$, $R^8$, $R^{20}$, $R^{21}$ are hydrogen; R, $R^3$, $R^5$ and $R^6$ are chlorine; A is $(CH_2)_f$ where f is 1; B and G are O, a is 1, and D is O; E is *—$CR^{20}R^{21}$C(=O)—; c and d are 0; X is aryl substituted with $R^{11}$ through $R^{15}$; providing the following compounds:

TABLE 1-continued

Phenylalkyl Substituted Cyclic Urea Derivatives

I-EE

| Cmpd. No | b | $R^{11}$ | $R^{12}$ | $R^{13}$ | $R^{14}$ | $R^{15}$ |
|---|---|---|---|---|---|---|
| 573 | 4 | H | H | H | H | H |
| 574 | 4 | Cl | H | H | H | H |
| 575 | 4 | H | Cl | H | H | H |
| 576 | 4 | H | H | Cl | H | H |
| 577 | 4 | Cl | Cl | H | H | H |
| 578 | 4 | Cl | H | Cl | H | H |
| 579 | 4 | Cl | H | H | Cl | H |
| 580 | 4 | Cl | H | H | H | Cl |
| 581 | 4 | H | Cl | Cl | H | H |
| 582 | 4 | H | Cl | H | Cl | H |
| 583 | 4 | $CF_3$ | H | H | H | H |
| 584 | 4 | H | $CF_3$ | H | H | H |
| 585 | 4 | H | H | $CF_3$ | H | H |
| 586 | 4 | $OCF_3$ | H | H | H | H |
| 587 | 4 | H | $OCF_3$ | H | H | H |
| 588 | 4 | H | H | $OCF_3$ | H | H |
| 589 | 4 | $CH_3$ | H | H | H | H |
| 590 | 4 | H | $CH_3$ | H | H | H |
| 591 | 4 | H | H | $CH_3$ | H | H |
| 592 | 4 | $CH_3$ | $CH_3$ | H | H | H |
| 593 | 4 | $CH_3$ | H | $CH_3$ | H | H |
| 594 | 4 | $CH_3$ | H | H | $CH_3$ | H |
| 595 | 4 | $CH_3$ | H | H | H | $CH_3$ |
| 596 | 4 | H | $CH_3$ | $CH_3$ | H | H |
| 597 | 4 | H | $CH_3$ | H | $CH_3$ | H |
| 598 | 4 | F | H | H | H | H |
| 599 | 4 | H | F | H | H | H |
| 600 | 4 | H | H | F | H | H |
| 601 | 4 | F | F | H | H | H |
| 602 | 4 | F | H | F | H | H |
| 603 | 4 | F | H | H | F | H |
| 604 | 4 | F | H | H | H | F |
| 605 | 4 | H | F | F | H | H |
| 606 | 4 | H | F | H | F | H |
| 607 | 4 | Br | H | H | H | H |
| 608 | 4 | H | Br | H | H | H |
| 609 | 4 | H | H | Br | H | H |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —C(=O)C(=O)—; c and d are 0; X is
aryl substituted with $R^{11}$ through $R^{15}$; providing the following compounds:

I-FF

| Cmpd. No | b | $R^{11}$ | $R^{12}$ | $R^{13}$ | $R^{14}$ | $R^{15}$ |
|---|---|---|---|---|---|---|
| 610 | 4 | H | H | H | H | H |
| 611 | 4 | Cl | H | H | H | H |
| 612 | 4 | H | Cl | H | H | H |
| 613 | 4 | H | H | Cl | H | H |
| 614 | 4 | Cl | Cl | H | H | H |
| 615 | 4 | Cl | H | Cl | H | H |
| 616 | 4 | Cl | H | H | Cl | H |
| 617 | 4 | Cl | H | H | H | Cl |
| 618 | 4 | H | Cl | Cl | H | H |
| 619 | 4 | H | Cl | H | Cl | H |
| 620 | 4 | $CF_3$ | H | H | H | H |
| 621 | 4 | H | $CF_3$ | H | H | H |
| 622 | 4 | H | H | $CF_3$ | H | H |
| 623 | 4 | $OCF_3$ | H | H | H | H |
| 624 | 4 | H | $OCF_3$ | H | H | H |
| 625 | 4 | H | H | $OCF_3$ | H | H |
| 626 | 4 | $CH_3$ | H | H | H | H |
| 627 | 4 | H | $CH_3$ | H | H | H |
| 628 | 4 | H | H | $CH_3$ | H | H |
| 629 | 4 | $CH_3$ | $CH_3$ | H | H | H |
| 630 | 4 | $CH_3$ | H | $CH_3$ | H | H |
| 631 | 4 | $CH_3$ | H | H | $CH_3$ | H |
| 632 | 4 | $CH_3$ | H | H | H | $CH_3$ |
| 633 | 4 | H | $CH_3$ | $CH_3$ | H | H |
| 634 | 4 | H | $CH_3$ | H | $CH_3$ | H |
| 635 | 4 | F | H | H | H | H |
| 636 | 4 | H | F | H | H | H |
| 637 | 4 | H | H | F | H | H |
| 638 | 4 | F | F | H | H | H |
| 639 | 4 | F | H | F | H | H |
| 640 | 4 | F | H | H | F | H |
| 641 | 4 | F | H | H | H | F |
| 642 | 4 | H | F | F | H | H |
| 643 | 4 | H | F | H | F | H |
| 644 | 4 | Br | H | H | H | H |
| 645 | 4 | H | Br | H | H | H |
| 646 | 4 | H | H | Br | H | H |

Where $R^1$, $R^2$, $R^4$ $R^7$, $R^8$ are hydrogen; R, $R^3$,
$R^5$ and $R^6$ are chlorine; A is $(CH_2)_f$ where f is 1; B and G are O,
a is 1, and D is O; E is —N=$CR^{20}$C(=O)—; c and d are 0; X is
aryl substituted with $R^{11}$ through $R^{15}$; providing the following compounds:

I-GG

| Cmpd. No | b | $R^{11}$ | $R^{12}$ | $R^{13}$ | $R^{14}$ | $R^{15}$ | $R^{20}$ |
|---|---|---|---|---|---|---|---|
| 647 | 4 | H | Cl | Cl | H | H | H |
| 648 | 4 | Cl | H | Cl | H | H | H |
| 649 | 4 | H | Cl | H | Cl | H | H |
| 650 | 4 | H | Cl | H | H | H | H |
| 651 | 4 | H | H | Cl | H | H | H |
| 652 | 4 | Cl | H | H | H | H | H |
| 653 | 4 | F | H | F | H | H | H |
| 654 | 4 | H | $OCH_3$ | Cl | H | H | H |
| 655 | 4 | H | H | $OCH_3$ | H | H | H |
| 656 | 4 | H | H | $OCF_2H$ | H | H | H |
| 657 | 4 | H | H | H | H | H | H |

Where R, $R^3$, $R^4$ $R^7$, $R^8$ are hydrogen; $R^1$, $R^2$,
$R^5$ and $R^6$ are chlorine; A is $(CH_2)_f$ where f is 1; B and G are O,
a is 1, and D is O; c and d are 0, X is aryl substituted with $R^{11}$
through $R^{15}$; providing the following compounds:

TABLE 1-continued

Phenylalkyl Substituted Cyclic Urea Derivatives

I-HH

| Cmpd. No | b | E | $R^{11}$ | $R^{12}$ | $R^{13}$ | $R^{14}$ | $R^{15}$ |
|---|---|---|---|---|---|---|---|
| 658 | 4 | *—N=CH— | H | F | H | F | H |
| 659 | 4 | —CH=CH— | H | H | H | $N(O^+)O^-$ | H |
| 660 | 4 | *—N=CH— | H | Cl | Cl | H | H |
| 661 | 4 | —N=N— | H | Cl | H | H | H |

*denotes attachment at 2 in formula I-HH

The following table sets forth physical characterizing data for certain compounds of formula I of the present invention. The test compounds of formula I are identified by numbers that correspond to those in Table 1:

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25

TABLE 2

Phenylalkyl Substituted Cyclic Urea Derivatives - Compound Characterization

| Cmpd. No. | Emperical Formulae | Melting Point (° C.) of Solids or Physical State | Cmpd. No. | Emperical Formulae | Melting Point (° C.) of Solids or Physical State |
|---|---|---|---|---|---|
| 4 | $C_{22}H_{19}Cl_5N_2O_3$ | Liquid | 41 | $C_{21}H_{18}Cl_5N_3O_3$ | Solid |
| 75 | $C_{21}H_{18}Cl_5N_3O_3$ | Oil | 76 | $C_{21}H_{17}Cl_6N_3O_3$ | Oil |
| 80 | $C_{21}H_{17}Cl_6N_3O_3$ | Oil | 81 | $C_{21}H_{17}Cl_6N_3O_3$ | Oil |
| 83 | $C_{25}H_{27}Cl_4N_3O_3$ | Oil | 86 | $C_{22}H_{21}Cl_4N_3O_3$ | Oil |
| 88 | $C_{22}H_{20}Cl_5N_3O_3$ | Oil | 87 | $C_{21}H_{17}Cl_4F_2N_3O_3$ | Oil |
| 89 | $C_{22}H_{18}Cl_4N_4O_3$ | Oil | 90 | $C_{21}H_{18}Cl_4IN_3O_3$ | Oil |
| 91 | $C_{21}H_{18}Cl_5N_3O_3$ | Oil | 92 | $C_{21}H_{18}Cl_5N_3O_3$ | Oil |
| 93 | $C_{21}H_{18}Cl_4N_4O_5$ | Oil | 94 | $C_{21}H_{19}Cl_4N_3O_3$ | Oil |
| 97 | $C_{22}H_{18}Cl_4F_3N_3O_4$ | Oil | 99 | $C_{23}H_{23}Cl_4N_3O_3$ | Oil |
| 100 | $C_{23}H_{23}Cl_4N_3O_3$ | Oil | 101 | $C_{22}H_{20}Cl_5N_3O_3$ | Oil |
| 104 | $C_{21}H_{18}BrCl_4N_3O_3$ | Oil | 105 | $C_{20}H_{14}Cl_4F_3N_3O_3$ | Oil |
| 106 | $C_{21}H_{16}Cl_4F_3N_3O_3$ | Oil | 107 | $C_{22}H_{18}Cl_4F_3N_3O_3$ | Solid; mp 84-86° C. |
| 110 | $C_{22}H_{21}Cl_4N_3O_3$ | Liquid | 113 | $C_{22}H_{20}Cl_5N_3O_3$ | Solid |
| 114 | $C_{22}H_{20}Cl_4FN_3O_3$ | Liquid | 118 | $C_{22}H_{19}Cl_6N_3O_3$ | Oil |
| 123 | $C_{22}H_{19}Cl_5FN_3O_3$ | Oil | 125 | $C_{26}H_{29}Cl_4N_3O_3$ | Oil |
| 131 | $C_{23}H_{20}Cl_4F_3N_3O_3$ | Oil | 135 | $C_{23}H_{21}Cl_4F_2N_3O_5S$ | Oil |
| 291 | $C_{21}H_{19}Cl_5N_4O_3$ | Liquid | 293 | $C_{24}H_{26}Cl_4N_4O_3$ | Liquid |
| 299 | $C_{21}H_{17}Cl_4F_3N_4O_3$ | Solid; mp 66-67° C. | 300 | $C_{20}H_{16}Cl_6N_4O_3$ | Liquid |
| 303 | $C_{20}H_{17}Cl_5N_4O_3$ | Solid; mp 72-74° C. | 304 | $C_{21}H_{17}Cl_4F_3N_4O_4$ | Solid; mp 83-84° C. |
| 306 | $C_{21}H_{17}Cl_4F_3N_4O_3$ | Oil | 307 | $C_{20}H_{16}Cl_6N_4O_3$ | Solid; mp 70-72° C. |
| 308 | $C_{20}H_{18}Cl_4N_4O_3$ | Liquid | 309 | $C_{18}H_{13}Cl_5N_4O_3$ | Oil |
| 311 | $C_{19}H_{15}Cl_5N_4O_3$ | Oil | 335 | $C_{24}H_{24}Cl_4N_4O_4$ | Liquid |
| 487 | $C_{21}H_{19}Cl_5N_4O_3$ | Solid | | | |
| 512 | $C_{21}H_{20}Cl_4N_4O_3$ | Liquid | 513 | $C_{21}H_{19}Cl_5N_4O_3$ | Liquid |
| 514 | $C_{21}H_{19}Cl_5N_4O_3$ | Liquid | 515 | $C_{21}H_{19}Cl_5N_4O_3$ | Liquid |
| 517 | $C_{21}H_{18}Cl_6N_4O_3$ | Liquid | 520 | $C_{21}H_{18}Cl_6N_4O_3$ | Liquid |
| 521 | $C_{21}H_{18}Cl_6N_4O_3$ | Liquid | 522 | $C_{19}H_{15}Cl_5N_4O_3$ | Liquid |
| 523 | $C_{20}H_{17}Cl_5N_4O_3$ | Liquid | | | |
| 536 | $C_{21}H_{20}Cl_4N_4O_4$ | Liquid | 546 | $C_{20}H_{16}Cl_6N_4O_3$ | Liquid |
| 547 | $C_{20}H_{17}Cl_5N_4O_3$ | Solid; mp 73-74° C. | 548 | $C_{20}H_{17}Cl_5N_4O_3$ | Liquid |
| 576 | $C_{22}H_{19}Cl_5N_2O_4$ | Oil | 613 | $C_{22}H_{17}Cl_5N_2O_5$ | Oil |
| 647 | $C_{22}H_{17}Cl_6N_3O_4$ | Oil | 648 | $C_{22}H_{17}Cl_6N_3O_4$ | Oil |
| 649 | $C_{22}H_{17}Cl_6N_3O_4$ | Oil | 650 | $C_{22}H_{18}Cl_5N_3O_4$ | Oil |
| 651 | $C_{22}H_{18}Cl_5N_3O_4$ | Oil | 652 | $C_{22}H_{18}Cl_5N_3O_4$ | Oil |
| 653 | $C_{22}H_{17}Cl_4F_2N_3O_4$ | Oil | 654 | $C_{23}H_{20}Cl_5N_3O_5$ | Oil |
| 655 | $C_{23}H_{21}Cl_4N_3O_5$ | Oil | 656 | $C_{23}H_{19}Cl_4F_2N_3O_5$ | Oil |
| 657 | $C_{22}H_{19}Cl_4N_3O_4$ | Oil | 658 | $C_{21}H_{17}Cl_4F_2N_3O_3$ | Oil |
| 659 | $C_{22}H_{19}Cl_4N_3O_5$ | Oil | 660 | $C_{21}H_{17}Cl_6N_3O_3$ | Oil |
| 661 | $C_{20}H_{17}Cl_5N_4O_3$ | Oil | | | | millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Certain Phenylalkyl Substituted Cyclic Urea Derivatives When Applied to the Surface of the Diet of Tobacco Budworm (*Heliothis virescens* [Fabricius])

| Cmpd. No. | Percent Mortality | Percent Growth Inhibition | Cmpd. No. | Percent Mortality | Percent Growth Inhibition |
|---|---|---|---|---|---|
| 4 | 100 | 100 | 41 | 100 | 100 |
| 75 | 100 | 100 | 76 | 100 | 100 |
| 80 | 100 | 100 | 81 | 100 | 100 |
| 83 | 100 | 100 | 86 | 100 | 100 |
| 88 | 100 | 100 | 87 | 100 | 100 |
| 89 | 100 | 100 | 90 | 100 | 100 |
| 91 | 100 | 100 | 92 | 100 | 100 |
| 93 | 100 | 100 | 94 | 100 | 100 |
| 97 | 100 | 100 | 99 | 100 | 100 |
| 100 | 100 | 100 | 101 | 100 | 100 |
| 104 | 100 | 100 | 105 | 100 | 100 |
| 106 | 100 | 100 | 107 | 100 | 100 |
| 110 | 100 | 100 | 113 | 100 | 100 |
| 114 | 100 | 100 | 118 | 100 | 100 |
| 123 | 100 | 100 | 125 | 100 | 100 |
| 131 | 100 | 100 | 135 | 100 | 100 |
| 291 | 100 | 100 | 293 | 100 | 100 |
| 299 | 100 | 100 | 300 | 100 | 100 |
| 303 | 100 | 100 | 304 | 100 | 100 |
| 306 | 100 | 100 | 307 | 100 | 100 |
| 308 | 100 | 100 | 309 | 100 | 100 |
| 311 | 100 | | 335 | 100 | 100 |
| 487 | 100 | 100 | | | |
| 512 | 100 | 100 | 513 | 100 | 100 |
| 514 | 100 | 100 | 515 | 100 | 100 |
| 517 | 100 | 100 | 520 | 0 | 58 |
| 521 | 100 | 100 | 522 | 50 | 100 |
| 523 | 100 | 100 | | | |
| 536 | 100 | 100 | 546 | 100 | 100 |
| 547 | 100 | 100 | 548 | 100 | 100 |
| 576 | 100 | 100 | 613 | 100 | 100 |
| 647 | 100 | 100 | 648 | 100 | 100 |
| 649 | 100 | 100 | 650 | 100 | 100 |
| 651 | 100 | 100 | 652 | 100 | 100 |

TABLE 3-continued

Insecticidal Activity of Certain Phenylalkyl Substituted Cyclic Urea Derivatives When Applied to the Surface of the Diet of Tobacco Budworm (*Heliothis virescens* [Fabricius])

| Cmpd. No. | Percent Mortality | Percent Growth Inhibition | Cmpd. No. | Percent Mortality | Percent Growth Inhibition |
|---|---|---|---|---|---|
| 653 | 100 | 100 | 654 | 100 | 100 |
| 655 | 100 | 100 | 656 | 100 | 100 |
| 657 | 100 | 100 | 658 | 100 | 100 |
| 659 | 100 | 100 | 660 | 100 | 100 |
| 661 | 100 | 100 | | | |

Concentration of the candidate insecticide on the surface of the diet is 0.25 millimolar As set forth in Table 3, all of the compounds of the present invention tested, except compound 25, provided 100% mortality and 100% growth inhibition of the tobacco budworm.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I

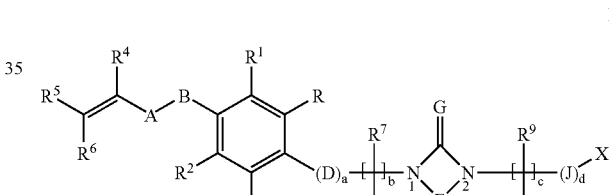

where

R and $R^3$ are independently selected from hydrogen and halogen;

$R^1$ and $R^2$ are independently selected from hydrogen, halogen and $(C_1$-$C_3)$alkyl;

A is $(CH_2)_f$ where f is 1;

B is O;

$R^4$ is hydrogen;

$R^5$ and $R^6$ are independently selected from halogen;

a is 1;

D is O;

b is an integer selected from 0, 1, 2, 3, 4, 5 or 6;

and when b is 1 or more, $R^7$ and $R^8$ are hydrogen;

E is a bridging group selected from —$CR^{20}$=$CR^{21}$—, *—$CR^{20}$=N—, *—N=$CR^{20}$—, —N=N—, *—C(=O)$CR^{20}R^{21}$—, *—$CR^{20}R^{21}$C(=O)—, —($CR^{20}R^{21}$)$_n$—, *—N=$CR^{20}$C(=O)—, *—C(=O)$CR^{20}$=N—, *—C(=O)$NR^{20}$—, *—$NR^{20}$C(=O)—, —C(=O)C(=O)—, and —C(=O)— where the asterisk denotes attachment at the position designated as 1 in formula I, n is an integer selected from 2, 3, and 4, and $R^{20}$ and $R^{21}$ are independently selected from hydrogen, and $(C_1$-$C_4)$alkyl;

G is O;

c is 0 or 1;

and when c is 1, $R^9$ and $R^{10}$ are hydrogen;

d is 0;

X is selected from a substituted aryl or a substituted heteroaryl, wherein the substituents are independently selected from hydrogen, halogen, $(C_1-C_6)$alkyl, $(C_2-C_4)$alkenyl, $(C_2-C_4)$alkynyl, halo$(C_1-C_6)$alkyl, halo$(C_1-C_6)$alkoxy, 4ydroxyl$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy$(C_1-C_6)$alkyl, $(C_2-C_4)$alkenyloxy, $(C_2-C_4)$alkynyloxy, halo$(C_1-C_6)$alkoxy, halo$(C_2-C_4)$alkenyloxy, halo$(C_2-C_4)$alkynyloxy, $(C_1-C_6)$alkylthio, pentahalothio, $(C_1-C_6)$alkylsulfinyl, $(C_1-C6)$alkylsulfonyl, halo$(C_1-C_6)$alkylthio, halo$(C_1-C_6)$alkylsulfinyl, halo$(C_1-C_6)$alkylsulfonyl, cyano, nitro; $NR^cR^d$, where $R^c$ and $R^d$ are independently selected from hydrogen, $(C_1-C_6)$alkyl, halo$(C_1-C_6)$alkyl, $(C_1-C_6)$alkylcarbonyl, and $(C_1-C_6)$alkoxycarbonyl, or where $R^c$ and $R^d$ may be taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$alkylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy; provided that when X is a substituted aryl having the following structure,

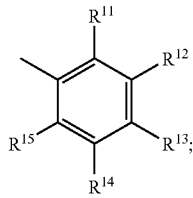

$R^{11}$ and $R^{12}$, or $R^{12}$ and $R^{13}$, or $R^{13}$ and $R^{14}$ or $R^{14}$ and $R^{15}$ are taken together with —$CR^{24}$=$CR^{25}CR^{26}$=$CR^{27}$—, —$OCR^{24}R^{25}CH_2$—, —$CH_2CR^{24}R^{25}O$—, —$OCR^{24}R^{25}O$—, —$OCR^{24}R^{25}CR^{26}R^{27}O$—, —$OCR^{24}R^{25}CH$=CH—, —$OCR^{24}R^{25}CH_2CH_2$—, —$OCR^{24}$=N—, —N=$CR^{24}$O—, —ON=$CR^{24}$—, —$ONR^{24}$C(=O)—, —$CH_2NR^{24}$C(=O)—, —$C_3H_6$—, —$C_2H_4$(C=O)—, —$SCR^{24}$=N—, —$OCR^{24}R^{25}$C(=O)—, —$CR^{24}$=$CR^{25}NR^{26}$—, —$CR^{24}$=$NNR^{25}$—, —N=$NNR^{24}$— or —N=$CR^{24}$N=N— to form a fused ring, where $R^{24}$ through $R^{27}$, inclusively, are independently selected from hydrogen, halogen, $(C_1-C_3)$alkyl, halo$(C_1-C_3)$alkyl, halo$(C_1-C_3)$alkoxy and aryl; and agriculturally-acceptable salts thereof.

2. A compound of claim 1, wherein R and $R^3$ are halogen; A is $(CH_2)_f$ where f is 1; B is O;

$R^5$ $R^6$ are independently selected from chlorine and bromine;

a is 1, and D is O;

b is an integer selected from 0, 1, 2, 3, 4, 5 or 6, and when b is 1 or more, $R^7$ and $R^8$ are each hydrogen;

E is said bridging group selected from —$CR^{20}$=$CR^{21}$—, *—$CR^{20}$=N—, *—N=$CR^{20}$— and —N=N—, where $R^{20}$ and $R^{21}$ are independently selected from hydrogen and $(C_1-C_4)$alkyl;

G is O;

c is 0 or 1, and $R^9$ and $R^{10}$ are each hydrogen;

d is 0; and

X is said substituted aryl or substituted heteroaryl wherein the substituents are independently selected from hydrogen, halogen, $(C_1-C_6)$alkyl, halo$(C_1-C_3)$alkyl, halo$(C_1-C_3)$alkoxy and halo$(C_1-C_6)$alkylsulfonyl; provided that when X is a substituted aryl having the following structure,

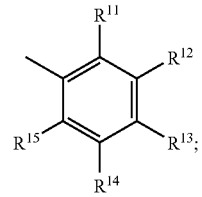

$R^{11}$ and $R^{12}$ or $R^{13}$ and $R^{14}$ may be taken together with —$OCR^{24}R^{25}CH_2$—, —$CH_2CR^{24}R^{25}O$—, —$CR^{24}$=$CR^{25}CR^{26}$=$CR^{27}$—, —$OCR^{24}R^{25}O$— or —$OCR^{24}$=N— to form a fused ring, where $R^{24}$, $R^{25}$, $R^{26}$ and $R^{27}$ are each hydrogen, chlorine, fluorine, $(C_1-C_3)$alkyl, halo$(C_1-C_3)$alkyl or halo$(C_1-C_3)$alkoxy.

3. A compound of claim 2, wherein R and $R^3$ are each chlorine; $R^1$ and $R^2$ are each hydrogen; a is 1 and D is O; b is an integer selected from 2, 3 or 4; E is said bridging group selected from —$CR^{20}$=N—, —N=$CR^{20}$— or —N=N—, where $R^{20}$ is selected from hydrogen or methyl; G is O; c is 0 or 1; d is 0; and X is a substituted aryl have the following structure,

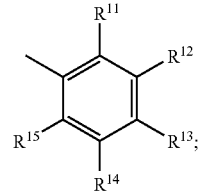

where $R^{11}$ through $R^{15}$, inclusively, are independently selected from hydrogen, halogen, $(C_1-C_6)$alkyl, halo$(C_1-C_3)$alkyl, halo$(C_1-C_3)$alkoxy and halo$(C_1-C_6)$alkylsulfonyl, and where $R^{11}$ and $R^{12}$ may be taken together with —$OCR^{24}R^{25}CH_2$—, —$OCR^{24}R^{25}O$— or —$OCR^{24}$=N— to form a fused ring, where $R^{24}$ and $R^{25}$ are selected from $(C_1-C_3)$alkyl and halo$(C_1-C_3)$alkyl.

4. A compound of claim 3, wherein $R^{11}$ through $R^{15}$, inclusively, are independently selected from hydrogen, chlorine, fluorine, 1,1-dimethylethyl, trifluoromethyl, and difluoromethylsulfonyl; and where $R^{11}$ and $R^{12}$ may be taken together with —$ORC^{24}R^{25}CH_2$—, —$OCR^{24}R^{25}O$— or —$OCR^{24}$=N— to form a fused ring, where $R^{24}$ and $R^{25}$ are each methyl or trifluoromethyl.

5. A compound of claim 3, wherein $R^{11}$ through $R^{15}$, inclusively, are independently selected from halogen or halo$(C_1-C_3)$alkyl; E is —N=N— and b is 4.

6. A compound of formula I-JJ

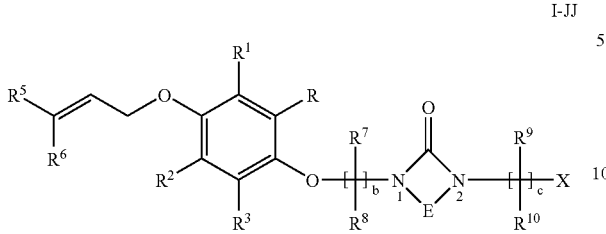

I-JJ where
R and $R^3$ are independently selected from halogen;
$R^1$ and $R^2$ are independently selected from hydrogen, halogen and $(C_1-C_3)$alkyl;
$R^5$ $R^6$ are independently selected from halogen;
b is an integer selected from 2, 3 or 4;
$R^7$ and $R^8$ are hydrogen;
E is a bridging group selected from *—$CR^{20}$=N—, *—N=$CR^{20}$— and —N=N— where the asterisk denotes attachment at the position designated as 1 in formula I-JJ, and $R^{20}$ is selected from hydrogen, and;
c is 0 or 1;
and when c is 1,
$R^9$ and $R^{10}$ are hydrogen;
X is selected from a substituted aryl or a substituted heteroaryl, wherein the substituents are independently selected from hydrogen, halogen, $(C_1-C_6)$alkyl, halo$(C_1-C_6)$alkyl and halo$(C_1-C_6)$alkoxy; and
agriculturally-acceptable salts thereof.

7. A compound of formula I-KK

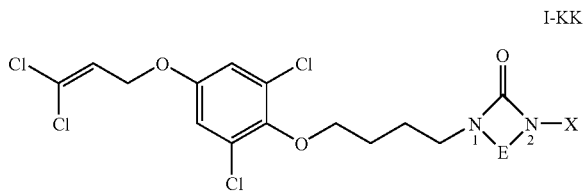

I-KK where
E is a bridging group selected from *—CH=N—, *—N=CH— and —N=N— where the asterisk denotes attachment at the position designated as 1 in formula I-KK;

X is selected from a substituted aryl wherein the substituents are independently selected from hydrogen, halogen, $(C_1-C_6)$alkyl, halo$(C_1-C_6)$alkyl and halo$(C_1-C_6)$alkoxy; and
agriculturally-acceptable salts thereof.

8. A composition comprising an insecticidally effective amount of a compound of claim 1 and at least one agriculturally acceptable extender or adjuvant.

9. A composition comprising an insecticidally effective amount of a compound of claim 6 and at least one agriculturally acceptable extender or adjuvant.

10. A composition comprising an insecticidally effective amount of a compound of claim 7 and at least one agriculturally acceptable extender or adjuvant.

11. The insecticidal composition of claim 8, further comprising one or more second compounds selected from the group consisting of pesticides, plant growth regulators, fertilizers and soil conditioners.

12. The insecticidal composition of claim 9, further comprising one or more second compounds selected from the group consisting of pesticides, plant growth regulators, fertilizers and soil conditioners.

13. The insecticidal composition of claim 10, further comprising one or more second compounds selected from the group consisting of pesticides, plant growth regulators, fertilizers and soil conditioners.

14. A method of controlling insects, comprising applying an insecticidally effective amount of a composition of claim 8 to a locus where insects are present or are expected to be present.

15. A method of controlling insects, comprising applying an insecticidally effective amount of a composition of claim 9 to a locus where insects are present or are expected to be present.

16. A method of controlling insects, comprising applying an insecticidally effective amount of a composition of claim 10 to a locus where insects are present or are expected to be present.

17. A method of controlling insects, comprising applying an insecticidally effective amount of a composition of claim 11 to a locus where insects are present or are expected to be present.

18. A method of controlling insects, comprising applying an insecticidally effective amount of a composition of claim 12 to a locus where insects are present or are expected to be present.

19. A method of controlling insects, comprising applying an insecticidally effective amount of a composition of claim 13 to a locus where insects are present or are expected to be present.

* * * * *

UNITED STATES PATENT AND TRADEMARK OFFICE
CERTIFICATE OF CORRECTION

| | | |
|---|---|---|
| PATENT NO. | : 7,713,970 B2 | Page 1 of 1 |
| APPLICATION NO. | : 11/569188 | |
| DATED | : May 11, 2010 | |
| INVENTOR(S) | : Edward J. Barron et al. | |

It is certified that error appears in the above-identified patent and that said Letters Patent is hereby corrected as shown below:

Column 47, line 25, insert --(C1-C4)alkyl-- after "hydrogen, and"

Signed and Sealed this
Twenty-eighth Day of June, 2011

David J. Kappos
*Director of the United States Patent and Trademark Office*